United States Patent
Thornbrue et al.

(10) Patent No.: US 10,716,989 B2
(45) Date of Patent: *Jul. 21, 2020

(54) SWING ANALYSIS METHOD USING A SWEET SPOT TRAJECTORY

(71) Applicant: Blast Motion Inc., Carlsbad, CA (US)

(72) Inventors: James Thornbrue, San Diego, CA (US); Patrick Cherveny, San Marcos, CA (US); Bhaskar Bose, Carlsbad, CA (US); Michael Bentley, Carlsbad, CA (US); Ryan Kaps, Mesa, AZ (US)

(73) Assignee: BLAST MOTION INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/189,889

(22) Filed: Nov. 13, 2018

(65) Prior Publication Data

US 2019/0076720 A1    Mar. 14, 2019

Related U.S. Application Data

(63) Continuation of application No. 15/628,613, filed on Jun. 20, 2017, now Pat. No. 10,124,230, which is a (Continued)

(51) Int. Cl.
*A63B 69/36* (2006.01)
*A63B 69/00* (2006.01)
(Continued)

(52) U.S. Cl.
CPC ...... *A63B 69/3685* (2013.01); *A63B 69/3635* (2013.01); *G01C 21/00* (2013.01);
(Continued)

(58) Field of Classification Search
USPC .................. 473/221–223, 257, 409, 453
See application file for complete search history.

(56) References Cited

U.S. PATENT DOCUMENTS

| 1,712,537 A | 5/1929 | White |
| 3,182,508 A | 5/1965 | Varju |

(Continued)

FOREIGN PATENT DOCUMENTS

| EP | 2025369 A2 | 2/2009 |
| EP | 247993 | 7/2012 |

(Continued)

OTHER PUBLICATIONS

International Search Report received in PCT/US2016/042668, dated Oct. 4, 2016, 21 pages.

(Continued)

*Primary Examiner* — Nini F Legesse
(74) *Attorney, Agent, or Firm* — Arc IP Law, PC; Joseph J. Mayo

(57) ABSTRACT

A method for analyzing sensor data from baseball swings (or swings in similar sports) that transforms data into a reference frame defined by the bat orientation and velocity at impact. The trajectory of the sweet spot of the bat is tracked through the swing, and is analyzed to generate metrics describing the swing. A two-lever model of the swing may be used to model the effects of body rotation and wrist rotation. Data may be analyzed to identify relevant events during the swing such as start of downswing, commit (wrist release), on-plane, peak bat speed, and impact. Illustrative swing metrics derived from the sweet spot trajectory, the swing plane reference frame, and the two-lever model include: forward bat speed, on-plane rotation, hinge angle at commit, hinge angle at impact, body rotation ratio, body tilt angle, and swing plane tilt angle.

30 Claims, 23 Drawing Sheets

Related U.S. Application Data continuation-in-part of application No. 15/214,339, filed on Jul. 19, 2016, now Pat. No. 9,694,267.

(51) Int. Cl.

| | |
|---|---|
| *G01C 21/16* | (2006.01) |
| *G01P 15/08* | (2006.01) |
| *G06K 9/00* | (2006.01) |
| *G01C 21/00* | (2006.01) |
| *G06F 19/00* | (2018.01) |
| *G06Q 10/06* | (2012.01) |
| *G06T 7/20* | (2017.01) |
| *G16H 20/30* | (2018.01) |

(52) U.S. Cl.
CPC .......... *G01C 21/16* (2013.01); *G01P 15/0888* (2013.01); *G06F 19/00* (2013.01); *G06F 19/3481* (2013.01); *G06K 9/00342* (2013.01); *G06K 9/00523* (2013.01); *G06K 9/00536* (2013.01); *G06Q 10/0639* (2013.01); *G06T 7/20* (2013.01); *A63B 2069/0008* (2013.01); *A63B 2220/18* (2013.01); *A63B 2220/833* (2013.01); *G16H 20/30* (2018.01)

(56) References Cited

U.S. PATENT DOCUMENTS

| | | |
|---|---|---|
| 3,226,704 A | 12/1965 | Petrash |
| 3,270,564 A | 9/1966 | Evans |
| 3,776,556 A | 12/1973 | McLaughlin |
| 3,788,647 A | 1/1974 | Evans |
| 3,792,863 A | 2/1974 | Evans |
| 3,806,131 A | 4/1974 | Evans |
| 3,945,646 A | 3/1976 | Hammond |
| 4,759,219 A | 7/1988 | Cobb et al. |
| 4,898,389 A | 2/1990 | Plutt |
| 4,902,014 A | 2/1990 | Bontomase et al. |
| 4,910,677 A | 3/1990 | Remedio et al. |
| 4,940,236 A | 7/1990 | Allen |
| 4,991,850 A | 2/1991 | Wilhlem |
| 5,056,783 A | 10/1991 | Matcovich et al. |
| 5,086,390 A | 2/1992 | Matthews |
| 5,111,410 A | 5/1992 | Nakayama et al. |
| 5,127,044 A | 6/1992 | Bonito et al. |
| 5,184,295 A | 2/1993 | Mann |
| 5,230,512 A | 7/1993 | Tattershall |
| 5,233,544 A | 8/1993 | Kobayashi |
| 5,249,967 A | 10/1993 | O'Leary et al. |
| 5,259,620 A | 11/1993 | Marocco |
| 5,283,733 A | 2/1994 | Colley |
| 5,298,904 A | 3/1994 | Olich |
| 5,332,225 A | 7/1994 | Ura |
| 5,333,061 A | 7/1994 | Nakashima et al. |
| 5,364,093 A | 11/1994 | Huston et al. |
| 5,372,365 A | 12/1994 | McTeigue et al. |
| 5,441,256 A | 8/1995 | Hackman |
| 5,441,269 A | 8/1995 | Henwood |
| 5,443,260 A | 8/1995 | Stewart et al. |
| 5,486,001 A | 1/1996 | Baker |
| 5,524,081 A | 6/1996 | Paul |
| 5,542,676 A | 8/1996 | Howe et al. |
| 5,592,401 A | 1/1997 | Kramer |
| 5,610,590 A | 3/1997 | Johnson et al. |
| 5,638,300 A | 6/1997 | Johnson |
| 5,665,006 A | 9/1997 | Pellegrini |
| 5,688,183 A | 11/1997 | Sabatino et al. |
| 5,694,340 A | 12/1997 | Kim |
| 5,707,299 A | 1/1998 | McKenna |
| 5,772,522 A | 6/1998 | Nesbit |
| 5,779,555 A | 7/1998 | Nomura et al. |
| 5,792,001 A | 8/1998 | Henwood |
| 5,819,206 A | 10/1998 | Horton |
| 5,826,578 A | 10/1998 | Curchod |
| 5,868,578 A | 2/1999 | Baum |
| 5,904,484 A | 5/1999 | Burns |
| 5,941,779 A | 8/1999 | Zeiner-Gundersen |
| 5,973,596 A | 10/1999 | French et al. |
| 5,993,333 A | 11/1999 | Heckaman |
| 5,998,968 A | 12/1999 | Pittman et al. |
| 6,012,995 A | 1/2000 | Martin |
| 6,030,109 A | 2/2000 | Lobsenz |
| 6,044,704 A | 4/2000 | Sacher |
| 6,073,086 A | 6/2000 | Marinelli |
| 6,224,493 B1 | 5/2001 | Lee et al. |
| 6,248,021 B1 | 6/2001 | Ognjanovic |
| 6,253,159 B1 | 6/2001 | Bett et al. |
| 6,254,492 B1 | 7/2001 | Taggett |
| 6,266,623 B1 | 7/2001 | Vock et al. |
| 6,293,802 B1 | 9/2001 | Ahlgren |
| 6,366,205 B1 | 4/2002 | Sutphen |
| 6,441,745 B1 | 8/2002 | Gates |
| 6,456,938 B1 | 9/2002 | Barnard |
| 6,537,076 B2 | 3/2003 | McNitt |
| 6,540,620 B1 | 4/2003 | Consiglio |
| 6,567,536 B2 | 5/2003 | McNitt |
| 6,582,328 B2 | 6/2003 | Kuta et al. |
| 6,611,141 B1 | 8/2003 | Schulz |
| 6,697,820 B1 | 2/2004 | Tarlie |
| 6,705,942 B1 | 3/2004 | Crook et al. |
| 6,746,336 B1 | 6/2004 | Brant et al. |
| 6,757,572 B1 | 6/2004 | Forest |
| 6,774,932 B1 | 8/2004 | Ewing et al. |
| 6,802,772 B1 | 10/2004 | Kunzle et al. |
| 6,868,338 B1 | 3/2005 | Elliott |
| 6,900,759 B1 | 5/2005 | Katayama |
| 6,908,404 B1 | 6/2005 | Gard |
| 6,923,729 B2 | 8/2005 | McGinty et al. |
| 7,004,848 B2 | 2/2006 | Konow |
| 7,021,140 B2 | 4/2006 | Perkins |
| 7,034,694 B2 | 4/2006 | Yamaguchi et al. |
| 7,037,198 B2 | 5/2006 | Hameen-Anttila |
| 7,092,846 B2 | 8/2006 | Vock et al. |
| 7,118,498 B2 | 10/2006 | Meadows et al. |
| 7,121,962 B2 | 10/2006 | Reeves |
| 7,143,639 B2 | 12/2006 | Gobush |
| 7,160,200 B2 | 1/2007 | Grober |
| 7,175,177 B2 | 2/2007 | Meifu et al. |
| 7,205,894 B1 | 4/2007 | Savage |
| 7,212,943 B2 | 5/2007 | Aoshima et al. |
| 7,219,033 B2 | 5/2007 | Kolen |
| 7,234,351 B2 | 6/2007 | Perkins |
| 7,264,554 B2 | 9/2007 | Bentley |
| 7,283,647 B2 | 10/2007 | McNitt |
| 7,421,369 B2 | 9/2008 | Clarkson |
| 7,433,805 B2 | 10/2008 | Vock et al. |
| 7,457,439 B1 | 11/2008 | Madsen |
| 7,457,724 B2 | 11/2008 | Vock et al. |
| 7,492,367 B2 | 2/2009 | Mahajan et al. |
| 7,494,236 B2 | 2/2009 | Lim |
| 7,499,828 B2 | 3/2009 | Barton |
| 7,561,989 B2 | 7/2009 | Banks |
| 7,623,987 B2 | 11/2009 | Vock et al. |
| 7,627,451 B2 | 12/2009 | Vock et al. |
| 7,689,378 B2 | 3/2010 | Kolen |
| 7,713,148 B2 | 5/2010 | Sweeney |
| 7,731,598 B1 | 6/2010 | Kim et al. |
| 7,736,242 B2 | 6/2010 | Stites et al. |
| 7,771,263 B2 | 8/2010 | Telford |
| 7,780,450 B2 | 8/2010 | Tarry |
| 7,800,480 B1 | 9/2010 | Joseph et al. |
| 7,813,887 B2 | 10/2010 | Vock et al. |
| 7,831,212 B1 | 11/2010 | Balardeta et al. |
| 7,871,333 B1 | 1/2011 | Davenport |
| 7,966,154 B2 | 6/2011 | Vock et al. |
| 7,983,876 B2 | 7/2011 | Vock et al. |
| 8,036,826 B2 | 10/2011 | MacIntosh et al. |
| 8,117,888 B2 | 2/2012 | Chan et al. |
| 8,172,722 B2 | 5/2012 | Molyneux et al. |
| 8,231,506 B2 | 7/2012 | Molyneux et al. |
| 8,249,831 B2 | 8/2012 | Vock et al. |
| 8,257,191 B2 | 9/2012 | Stites et al. |
| 8,282,487 B2 | 10/2012 | Wilson et al. |
| 8,314,840 B1 | 11/2012 | Funk |

(56) References Cited

U.S. PATENT DOCUMENTS

| | | |
|---|---|---|
| 8,352,211 B2 | 1/2013 | Vock et al. |
| 8,400,548 B2 | 3/2013 | Bilbrey et al. |
| 8,425,292 B2 | 4/2013 | Lui et al. |
| 8,477,027 B2 | 7/2013 | Givens |
| 8,527,228 B2 | 9/2013 | Panagas |
| 8,565,483 B2 | 10/2013 | Nakaoka |
| 8,589,114 B2 | 11/2013 | Papadourakis |
| 8,696,482 B1 | 4/2014 | Pedenko et al. |
| 8,723,986 B1 | 5/2014 | Merrill |
| 8,725,452 B2 | 5/2014 | Han |
| 8,764,576 B2 | 7/2014 | Takasugi |
| 8,781,610 B2 | 7/2014 | Han |
| 8,831,905 B2 | 9/2014 | Papadourakis |
| 8,876,621 B2 | 11/2014 | Shibuya |
| 8,888,603 B2 | 11/2014 | Sato et al. |
| 8,905,856 B2 | 12/2014 | Parke et al. |
| 8,929,709 B2 | 1/2015 | Lokshin |
| 8,944,932 B2 | 2/2015 | Sato et al. |
| 8,944,939 B2 | 2/2015 | Clark et al. |
| 8,956,238 B2 | 2/2015 | Boyd et al. |
| 8,988,341 B2 | 3/2015 | Lin et al. |
| 8,989,441 B2 | 3/2015 | Han et al. |
| 9,032,794 B2 | 5/2015 | Perkins et al. |
| 9,060,682 B2 | 6/2015 | Lokshin |
| 9,146,134 B2 | 9/2015 | Lokshin et al. |
| 9,646,199 B2 * | 5/2017 | Bose .................. G11B 27/17 |
| 9,656,122 B2 | 5/2017 | Papadourakis |
| 9,694,267 B1 * | 7/2017 | Thornbrue ......... A63B 69/0002 |
| 10,124,230 B2 * | 11/2018 | Thornbrue ............. G01C 21/00 |
| 2001/0029207 A1 | 10/2001 | Cameron et al. |
| 2001/0035880 A1 | 11/2001 | Musatov et al. |
| 2001/0045904 A1 | 11/2001 | Silzer, Jr. |
| 2001/0049636 A1 | 12/2001 | Hudda et al. |
| 2002/0004723 A1 | 1/2002 | Meifu et al. |
| 2002/0019677 A1 | 2/2002 | Lee |
| 2002/0049507 A1 | 4/2002 | Hameen-Anttila |
| 2002/0052750 A1 | 5/2002 | Hirooka |
| 2002/0064764 A1 | 5/2002 | Fishman |
| 2002/0072815 A1 | 6/2002 | McDonough et al. |
| 2002/0077189 A1 | 6/2002 | Tuer et al. |
| 2002/0082775 A1 | 6/2002 | Meadows et al. |
| 2002/0115046 A1 | 8/2002 | McNitt et al. |
| 2002/0126157 A1 | 9/2002 | Farago et al. |
| 2002/0151994 A1 | 10/2002 | Sisco |
| 2002/0173364 A1 | 11/2002 | Boscha |
| 2002/0177490 A1 | 11/2002 | Yong et al. |
| 2002/0188359 A1 | 12/2002 | Morse |
| 2003/0008722 A1 | 1/2003 | Konow |
| 2003/0073518 A1 | 4/2003 | Marty |
| 2003/0074659 A1 | 4/2003 | Louzoun |
| 2003/0109322 A1 | 6/2003 | Funk et al. |
| 2003/0163287 A1 | 8/2003 | Vock et al. |
| 2003/0191547 A1 | 10/2003 | Morse |
| 2003/0208830 A1 | 11/2003 | Marmaropoulos |
| 2004/0028258 A1 | 2/2004 | Naimark et al. |
| 2004/0033843 A1 | 2/2004 | Miller |
| 2004/0044493 A1 | 3/2004 | Coulthard |
| 2004/0147329 A1 | 7/2004 | Meadows et al. |
| 2004/0227676 A1 | 11/2004 | Kim et al. |
| 2004/0248676 A1 | 12/2004 | Taylor |
| 2005/0021292 A1 | 1/2005 | Vock et al. |
| 2005/0023763 A1 | 2/2005 | Richardson |
| 2005/0032582 A1 | 2/2005 | Mahajan et al. |
| 2005/0054457 A1 | 3/2005 | Eyestone et al. |
| 2005/0156068 A1 | 7/2005 | Ivans |
| 2005/0203430 A1 | 9/2005 | Williams et al. |
| 2005/0213076 A1 | 9/2005 | Saegusa |
| 2005/0215340 A1 | 9/2005 | Stites et al. |
| 2005/0227775 A1 | 10/2005 | Cassady et al. |
| 2005/0261073 A1 | 11/2005 | Farrington, Jr. et al. |
| 2005/0268704 A1 | 12/2005 | Bissonnette et al. |
| 2005/0272516 A1 | 12/2005 | Gobush |
| 2005/0282650 A1 | 12/2005 | Miettinen et al. |
| 2005/0288119 A1 | 12/2005 | Wang et al. |
| 2006/0020177 A1 | 1/2006 | Seo et al. |
| 2006/0025229 A1 | 2/2006 | Mahajan et al. |
| 2006/0038657 A1 | 2/2006 | Denison et al. |
| 2006/0063600 A1 | 3/2006 | Grober |
| 2006/0068928 A1 | 3/2006 | Nagy |
| 2006/0084516 A1 | 4/2006 | Eyestone et al. |
| 2006/0109116 A1 | 5/2006 | Keays |
| 2006/0122002 A1 | 6/2006 | Konow |
| 2006/0166738 A1 | 7/2006 | Eyestone et al. |
| 2006/0189389 A1 | 8/2006 | Hunter et al. |
| 2006/0199659 A1 | 9/2006 | Caldwell |
| 2006/0247070 A1 | 11/2006 | Funk et al. |
| 2006/0250745 A1 | 11/2006 | Butler et al. |
| 2006/0270450 A1 | 11/2006 | Garratt et al. |
| 2006/0276256 A1 | 12/2006 | Storek |
| 2006/0284979 A1 | 12/2006 | Clarkson |
| 2006/0293112 A1 | 12/2006 | Yi |
| 2007/0052807 A1 | 3/2007 | Zhou et al. |
| 2007/0062284 A1 | 3/2007 | Machida |
| 2007/0081695 A1 | 4/2007 | Foxlin et al. |
| 2007/0087866 A1 | 4/2007 | Meadows et al. |
| 2007/0099715 A1 | 5/2007 | Jones et al. |
| 2007/0111811 A1 | 5/2007 | Grober |
| 2007/0129178 A1 | 6/2007 | Reeves |
| 2007/0135225 A1 | 6/2007 | Nieminen |
| 2007/0135237 A1 | 6/2007 | Reeves |
| 2007/0219744 A1 | 9/2007 | Kolen |
| 2007/0265105 A1 | 11/2007 | Barton |
| 2007/0270214 A1 | 11/2007 | Bentley |
| 2007/0298896 A1 | 12/2007 | Nusbaum |
| 2008/0027502 A1 | 1/2008 | Ransom |
| 2008/0085778 A1 | 4/2008 | Dugan |
| 2008/0090703 A1 | 4/2008 | Rosenberg |
| 2008/0108456 A1 | 5/2008 | Bonito |
| 2008/0164999 A1 | 7/2008 | Otto |
| 2008/0182685 A1 | 7/2008 | Marty et al. |
| 2008/0190202 A1 | 8/2008 | Kulach et al. |
| 2008/0211768 A1 | 9/2008 | Breen et al. |
| 2008/0234935 A1 | 9/2008 | Wolf et al. |
| 2008/0280642 A1 | 11/2008 | Coxhill et al. |
| 2008/0284979 A1 | 11/2008 | Yee et al. |
| 2008/0285805 A1 | 11/2008 | Luinge et al. |
| 2009/0002316 A1 | 1/2009 | Rofougaran |
| 2009/0017944 A1 | 1/2009 | Savarese et al. |
| 2009/0029754 A1 | 1/2009 | Slocum et al. |
| 2009/0033741 A1 | 2/2009 | Oh et al. |
| 2009/0036237 A1 | 2/2009 | Nipper et al. |
| 2009/0048044 A1 | 2/2009 | Oleson et al. |
| 2009/0055820 A1 | 2/2009 | Huang |
| 2009/0088276 A1 | 4/2009 | Solheim et al. |
| 2009/0111602 A1 | 4/2009 | Savarese et al. |
| 2009/0131190 A1 | 5/2009 | Kimber |
| 2009/0137333 A1 | 5/2009 | Lin et al. |
| 2009/0144785 A1 | 6/2009 | Walker et al. |
| 2009/0174676 A1 | 7/2009 | Westerman |
| 2009/0177097 A1 | 7/2009 | Ma et al. |
| 2009/0191846 A1 | 7/2009 | Shi |
| 2009/0209343 A1 | 8/2009 | Foxlin et al. |
| 2009/0209358 A1 | 8/2009 | Niegowski |
| 2009/0213134 A1 | 8/2009 | Stephanick et al. |
| 2009/0222163 A1 | 9/2009 | Plante |
| 2009/0233735 A1 | 9/2009 | Savarese et al. |
| 2009/0254971 A1 | 10/2009 | Herz et al. |
| 2009/0299232 A1 | 12/2009 | Lanfermann et al. |
| 2010/0049468 A1 | 2/2010 | Papadourakis |
| 2010/0062869 A1 | 3/2010 | Chung et al. |
| 2010/0063778 A1 | 3/2010 | Schrock et al. |
| 2010/0063779 A1 | 3/2010 | Schrock et al. |
| 2010/0091112 A1 | 4/2010 | Veeser et al. |
| 2010/0093458 A1 | 4/2010 | Davenport et al. |
| 2010/0099509 A1 | 4/2010 | Ahem et al. |
| 2010/0103269 A1 | 4/2010 | Wilson et al. |
| 2010/0113174 A1 | 5/2010 | Ahern |
| 2010/0121227 A1 | 5/2010 | Stirling et al. |
| 2010/0121228 A1 | 5/2010 | Stirling et al. |
| 2010/0130298 A1 | 5/2010 | Dugan et al. |
| 2010/0144414 A1 | 6/2010 | Edis et al. |
| 2010/0144456 A1 | 6/2010 | Ahern |
| 2010/0144457 A1 | 6/2010 | Kim |
| 2010/0178994 A1 | 7/2010 | Do et al. |

(56) References Cited

U.S. PATENT DOCUMENTS

| | | |
|---|---|---|
| 2010/0201512 A1 | 8/2010 | Stirling et al. |
| 2010/0204616 A1 | 8/2010 | Shears et al. |
| 2010/0216564 A1 | 8/2010 | Stites et al. |
| 2010/0222152 A1 | 9/2010 | Jaekel et al. |
| 2010/0308105 A1 | 12/2010 | Savarese et al. |
| 2010/0309097 A1 | 12/2010 | Raviv et al. |
| 2010/0323794 A1 | 12/2010 | Su |
| 2011/0004871 A1 | 1/2011 | Liu |
| 2011/0029235 A1 | 2/2011 | Berry |
| 2011/0037778 A1 | 2/2011 | Deng et al. |
| 2011/0050864 A1 | 3/2011 | Bond |
| 2011/0052005 A1 | 3/2011 | Selner |
| 2011/0053688 A1 | 3/2011 | Crawford |
| 2011/0075341 A1 | 3/2011 | Lau et al. |
| 2011/0081981 A1 | 4/2011 | Okamoto |
| 2011/0126184 A1 | 5/2011 | Lisboa |
| 2011/0165998 A1 | 7/2011 | Lau et al. |
| 2011/0195780 A1 | 8/2011 | Lu |
| 2011/0230273 A1 | 9/2011 | Niegowski et al. |
| 2011/0230274 A1 | 9/2011 | Lafortune et al. |
| 2011/0230985 A1 | 9/2011 | Niegowski et al. |
| 2011/0230986 A1 | 9/2011 | Lafortune |
| 2011/0238308 A1 | 9/2011 | Miller et al. |
| 2011/0305369 A1* | 12/2011 | Bentley .............. G06K 9/00342 382/103 |
| 2012/0004034 A1 | 1/2012 | Pope et al. |
| 2012/0023354 A1 | 1/2012 | Chino |
| 2012/0052972 A1 | 3/2012 | Bentley |
| 2012/0088544 A1 | 4/2012 | Bentley et al. |
| 2012/0115626 A1 | 5/2012 | Davenport |
| 2012/0115682 A1 | 5/2012 | Homsi |
| 2012/0116548 A1 | 5/2012 | Goree et al. |
| 2012/0120572 A1 | 5/2012 | Bentley |
| 2012/0142415 A1 | 6/2012 | Lindsay |
| 2012/0157241 A1 | 6/2012 | Nomura et al. |
| 2012/0179418 A1 | 7/2012 | Takasugi et al. |
| 2012/0179742 A1 | 7/2012 | Acharya et al. |
| 2012/0191405 A1 | 7/2012 | Molyneux et al. |
| 2012/0295726 A1 | 11/2012 | Cherbini |
| 2012/0316004 A1 | 12/2012 | Shibuya |
| 2013/0029791 A1 | 1/2013 | Rose et al. |
| 2013/0095924 A1 | 4/2013 | Geisner et al. |
| 2013/0095941 A1 | 4/2013 | Bentley et al. |
| 2013/0110415 A1 | 5/2013 | Davis et al. |
| 2013/0128022 A1 | 5/2013 | Bose et al. |
| 2013/0173212 A1 | 7/2013 | Saiki et al. |
| 2013/0178304 A1 | 7/2013 | Chan |
| 2013/0191063 A1 | 7/2013 | Nomura |
| 2013/0225309 A1 | 8/2013 | Bentley et al. |
| 2013/0245966 A1 | 9/2013 | Burroughs et al. |
| 2013/0267335 A1 | 10/2013 | Boyd et al. |
| 2013/0271602 A1 | 10/2013 | Bentley et al. |
| 2013/0298668 A1 | 11/2013 | Sato |
| 2013/0319113 A1 | 12/2013 | Mizuta |
| 2013/0330054 A1 | 12/2013 | Lokshin |
| 2013/0332004 A1 | 12/2013 | Gompert et al. |
| 2013/0343729 A1 | 12/2013 | Rav-Acha et al. |
| 2013/0346013 A1 | 12/2013 | Lokshin |
| 2014/0019083 A1 | 1/2014 | Nakaoka |
| 2014/0100048 A1 | 4/2014 | Ota et al. |
| 2014/0100049 A1 | 4/2014 | Ota et al. |
| 2014/0100050 A1 | 4/2014 | Ota et al. |
| 2014/0135139 A1 | 5/2014 | Shibuya et al. |
| 2014/0156214 A1 | 6/2014 | Nomura |
| 2014/0172873 A1 | 6/2014 | Varoglu et al. |
| 2014/0200092 A1 | 7/2014 | Parke et al. |
| 2014/0200094 A1 | 7/2014 | Parke et al. |
| 2014/0213382 A1* | 7/2014 | Kang ................ A63B 69/3632 473/223 |
| 2014/0229135 A1 | 8/2014 | Nomura |
| 2014/0229138 A1 | 8/2014 | Goree et al. |
| 2014/0257743 A1 | 9/2014 | Lokshin et al. |
| 2014/0257744 A1 | 9/2014 | Lokshin et al. |
| 2014/0295982 A1* | 10/2014 | Shibuya ............... G09B 19/003 473/212 |
| 2014/0334796 A1 | 11/2014 | Galant et al. |
| 2014/0376876 A1 | 12/2014 | Bentley et al. |
| 2014/0378239 A1 | 12/2014 | Sato et al. |
| 2014/0379293 A1 | 12/2014 | Sato |
| 2014/0379294 A1 | 12/2014 | Shibuya et al. |
| 2014/0379295 A1 | 12/2014 | Sato et al. |
| 2015/0007658 A1 | 1/2015 | Ishikawa et al. |
| 2015/0012240 A1 | 1/2015 | Sato |
| 2015/0042481 A1 | 2/2015 | Nomura |
| 2015/0098688 A1 | 4/2015 | Lokshin |
| 2015/0124048 A1 | 5/2015 | King |
| 2015/0131845 A1 | 5/2015 | Forouhar et al. |
| 2015/0154452 A1* | 6/2015 | Bentley .............. G06K 9/00711 386/201 |
| 2015/0256689 A1 | 9/2015 | Erkkila et al. |
| 2015/0348591 A1* | 12/2015 | Kaps .................... G11B 27/17 386/201 |
| 2017/0061817 A1* | 3/2017 | Mettler May ........ G09B 19/003 |
| 2018/0021648 A1* | 1/2018 | Thornbrue .......... A63B 69/0002 473/453 |
| 2018/0021653 A1* | 1/2018 | Thornbrue .......... G06F 19/3481 473/453 |
| 2018/0070056 A1 | 3/2018 | DeAngelis et al. |

FOREIGN PATENT DOCUMENTS

| | | |
|---|---|---|
| EP | 2652738 | 10/2013 |
| EP | 2781240 | 9/2014 |
| JP | 2002210055 A | 7/2002 |
| JP | 2004207985 | 7/2004 |
| JP | 2005176030 | 6/2005 |
| JP | 2011000367 | 1/2011 |
| JP | 2012196241 | 10/2012 |
| JP | 2013188426 | 9/2013 |
| KR | 10-20030085275 | 11/2003 |
| KR | 10-20060041060 | 5/2006 |
| KR | 10-20070119018 | 12/2007 |
| KR | 10-20100074068 | 7/2010 |
| KR | 101079319 | 6/2011 |
| KR | 10-20100020131 | 9/2011 |
| WO | 1994027683 | 12/1994 |
| WO | 2007130057 A1 | 11/2007 |
| WO | 2009056688 A1 | 5/2009 |
| WO | 2011057194 | 5/2011 |
| WO | 2014085744 | 10/2012 |

OTHER PUBLICATIONS

International Search Report received in PCT/US2016/042671, dated Oct. 13, 2016, 17 pages.
International Search Report and Written Opinion received in PCT/US2016/042676, dated Oct. 24, 2016 (12 pages).
International Preliminary Report on Patentability received in PCT/US2015/026917, dated Nov. 3, 2016 (5 pages).
International Search Report received for PCT Application No. PCT/US2012/065716 dated Jan. 3, 2013, 10 pages.
myCaddie, 2009, retrieved on Sep. 26, 2012 from http://www.iMakePars.com, 4 pages.
Swing it See it Fiz it, Improve Gold Swing, SwingSmart Golf Analyzer, retrieved on Sep. 26, 2012 from http://www.SwingSmart.com, 2 pages.
Learn how Swingbyte can improve your game, retrieved on Sep. 26, 2012 from http://www.swingbyte.com, 2 pages.
International Search Report received for PCT Application No. PCT/US2011/055173, dated Mar. 6, 2012, 8 pages.
International Search Report received for PCT Application No. PCT/US2011/049461, dated Feb. 23, 2012, 14 pages, 2012.
PCT Search Report, PCT/US2012/029310, dated Sep. 28, 2012, 3 pages.
IPRP, PCT/US2011/049461, dated Mar. 7, 2013, 6 pages.
IPRP, PCT/US2011/058182, dated Apr. 30, 2013, 5 pages.
IPER, PCT/US2011/055173, dated Apr. 25, 2013, 5 pages, (2013).
IPRP, PCT/US2012/065716, dated May 20, 2014, 6 pages.
International Search Report for PCT Application No. PCT/US2013/021999, dated Apr. 30, 2013, 8 pages.

(56) References Cited

OTHER PUBLICATIONS

International Search Report for PCT Application No. PCT/US2012/066915, dated Mar. 29, 2013, 10 pages.
International Search Report for PCT Application No. PCT/US2015/26896, dated Jul. 28, 2015, 15 pages.
International Search Report for PCT Application No. PCTUS2015/26917, dated Jul. 30, 2015, 16 pages.
The Nike+FuelBand User's Guide, rev 14, 26 pages, 2012.
UP by Jawbone Extended User Guide, 10 pages, 2012.
Armour39, Under Armour Guarantee, Getting Started, retrieved from the Internet on Jul. 12, 2013, 7 pages.
Armour39 Module & Chest Strap, retrieved from the Internet on Jul. 12, 2013, 6 pages.
miCoach Pacer User Manual, 31 pages, (2009).
Foreman et al. "A Comparative Analysis for the Measurement of Head Accelerations in Ice Hockey Helmets using Non-Accelerometer Based Systems," Nov. 19, 2012, 13 pages.
Reebok-CCM and MC10 to Launch Revolutionary Sports Impact Indicator, MC10 News (http://www.mc10inc.com/news/), Oct. 24, 2012, 3 pages.
CheckLight MC10 Overview, Reebok International Limited, Nov. 20, 2012, 7 pages.
Reebok and MC10 Team Up to Build CheckLight, a Head Impact Indicator (Hands-on), MC10 News (http://www.mc10inc.com/news/), Jan. 11, 2013, 1 pg.
Trace—the Most Advanced Activity Monitor for Action Sports, webpage, retrieved on Aug. 6, 2013, 22 pages.
CheckLight, Sports/Activity Impact Indicator, User Manual, 13 pages, 2013, Reebok International Limited.
King, the Design and Application of Wireless Mems Inertial Measurement Units for the Measurement and Analysis of Golf Swings, 2008.
Grober, an Accelerometer Based Instrumentation of the Golf Club: Comparative Analysis of Golf Swings, 2009.
Gehrig et al, Visual Golf Club Tracking for Enhanced Swing Analysis, Computer Vision Lab, Lausanne, Switzerland, 2003.
Pocketpro Golf Designs, PocketPro Full Swing Analysis in Your Pocket, www.PocketPro.org, (2011).
Clemson University, Golf Shot Tutorial, http://www.webnucleo.org/home/onlinetools/newton/0.4/html/aboutthistool/tutorials/golf1.shp.cgi, retrieved on Nov. 10, 2011.
miCoach Speed Cell TM, User Manual, 23 pages, (2011).
Nike+iPod, User Guide, 32 pages (2010).
SureShotGPS SS9000X, Intelligent Touch, Instruction Manual, 25 pages, 2011.
ActiveReplay, "TRACE—the Most Advanced Activity Monitor for Action Sports", http://www.kickstarter.com/projects/activereplay/trace-the-most-advanced-activity-monitor-for-actio, 13 pages, Oct. 1, 2013.
Zepp Golfsense@Launch2011, https://www.youtube.com/watch?v=VnOcu8szjIk (video), Mar. 14, 2011.
Epson US Newsroom, "Epson America Enters Sports Wearables Market with Introduction of M-Tracer MT500GII Golf Swing Analyzer", www.news.epson.com, Jan. 05, 2015, 4 pages.
International Search Report and Written Opinion dated Dec. 22, 2015 received in PCTUS1561695, 7 pages.
Search Report Received in PCT2013021999 dated Jan. 21, 2016.
Patent Examination Report received in Australia Application No. 2011313952, dated Mar. 15, 2016, 5 pages.
"About Banjo" webpages retrieved from internet, dated 2015.
International Search Report and Written Opinion mailed in PCTU.S. Pat. No.1642674 on Aug. 12, 2016, 9 pages.
International Preliminary Report on Patentability in PCTUS2015061695, on Jun. 1, 2017, 5 pages.
European Search Report received in PCTUS2015026896 on May 11, 2017, 13 pages.
International Search Report and Written Opinion received in PCT/US2017/52114, dated Oct. 3, 9 pages.
International Search Report and Written Opinion Received in PCT/US2017/37987, dated Nov. 9, 2017, 12 pages.
Supplementary Extended European Search Report received in 11820763.8 dated Nov. 13, 2017, 16 pages.
Supplementary Extended European Search Report received in 11833159.4 dated Nov. 6, 2017, 14 pages.
Supplementary Partial European Search Report received from EP Application Serial No. 11820763.8, dated Aug. 8, 2017, 15 pages.
Supplementary Partial European Search Report received from EP Application Serial No. 11833159.4, dated Aug. 8, 2017, 15 pages.
Supplemental Search Report Received from Ep Application Serial No. 16825295.5, dated Jun. 6, 2019, 7 pages.
David E. Culler, Et al., "Smart Sensors to Network the World", published in Scientific American Magazine, No. 6/2004, dated Jun. 1, 2004, pp. 85-91.
International Search Report and Written Opinion received in PCT/US2017/039209, dated Aug. 24, 2017, 7 pages.
*Zepp Labs, Inc. v. Blast Motion, Inc.* Petition for Inter Partes Review of U.S. Pat. No. 8,903,521 filed on Feb. 24, 2016, as IPR2016-00672, and accompanying Declaration of Dr. Steven M. Nesbit.
*Zepp Labs, Inc. v. Blast Motion, Inc.* Petition for Inter Partes Review of U.S. Pat. No. 9,039,527 filed on Feb. 24, 2016, as IPR2016-00674, and accompanying Declaration of Dr. Steven M. Nesbit.
*Zepp Labs, Inc. v. Blast Motion, Inc.* Petition for Inter Partes Review of U.S. Pat. No. 8,941,723 filed on Feb. 24, 2016, as IPR2016-00675, and accompanying Declaration of Dr. Steven M. Nesbit.
*Zepp Labs, Inc. v. Blast Motion, Inc.* Petition for Inter Partes Review of U.S. Pat. No. 8,905,855 filed on Feb. 24, 2016, as IPR2016-00676, and accompanying Declaration of Dr. Steven M. Nesbit.
*Zepp Labs, Inc. v. Blast Motion, Inc.* Petition for Inter Partes Review of U.S. Pat. No. 8,944,928 filed on Feb. 24, 2016, as IPR2016-00677, and accompanying Declaration of Dr. Steven M. Nesbit.
Chris Otto, et al, "System Architecture of a Wireless Body Area Sensor Network for Ubiquitous Health Monitoring", *Journal of Mobile Multimedia*, vol. 1, No. 4, Jan. 10, 2006, University of Alabama in Huntsville, 20 pages.
Linx Technologies "High Performance RF Module: Hp3 Series Transmitter Module Data Guide Description", Jul. 27, 2011, 13 pages.
Roger Allan, "Wireless Sensor Architectures Uses Bluetooth Standard", ww.v.electronicdesign.com/e0111.111tmicationslwireless-sensor-architecture-uses-bitletooth-standard, Aug. 7, 2000, 5 pages.
Don Tuite, "Motion-Sensing MEMS Gyros and Accelerometers are Everywhere", www.electronicdesitm.com/print/analoglinotion-sensing-raems-vms-and-aceelerometers-are-evervwhere, Jul. 9, 2009, 6 pages.
InvenSense News Release, "InvenSense Unveils World's 1st IMU Solution for Consumer Applications", ir.invensense.com, 2016, 2 Pages.
Dean Takahashi, "Facebook, Twitter, Last.fm coming to Xbox Live this Fall", Jun. 1, 2009, Webpage printout, 5 pages.
The iClub System, Products pages, wwiclub.net, 2001-2005, 5 pages.
Websters New College Dictionary, Definition of "Virtual Reality", Third Edition, 2005, 3 pages.
SmartSwing, "SmartSwing Introduces Affordable Intelligent Golf Club", www.smartswinggolf.com , Jan. 2006, 2 pages.
Henrick Arfwedson, et al., "Ericsson's Bluetooth modules", Ericsson Review No. 4, 1999, 8 pages.
ZigBees, "Zigbee information", www.zisbees com, 2015, 4 pages.
SolidState Technology, "MEMS enable smart golf clubs", www eledroiq.com , 2005, 3 pages.
IGN, "Japanese Wii Price Release Date Revealed", www.ign com , 2006, 1 page.
First Annual Better Golf Through Technology Conference 2006 webpage, www.bettergolfthroughtechnology.com, Massachusetts Institute of Technology, Cambridge Massachusetts, Feb. 2006, 1 page.
Concept2Rowing, "Training" web content, www.concept2.com, 2009, 1 page.
Expresso, Products pages, www.expresso.com/products , 2009, 2 pages.
Manish Kalia, et al., "Efficient Policies for Increasing Capacity in Bluetooth: an Indoor Pico-Cellular Wireless System", IBM India Research Laboratory, Indian Institute of Technology, 2000, 5 pages.

(56) References Cited

OTHER PUBLICATIONS

R. Rao, et al., "Demand-Based Bluetooth Scheduling", Pennsylvania State University, 2001, 13 pages.
Supplementary Extended European Search Report received in 15782595.1 dated Nov. 27, 2017, 5 pages.
Supplementary European Search Report received in 15860384.5 dated Jun. 21, 2018, 9 pages.
International Search Report and Written Opinion received in PCT/US18033757, dated Aug. 31, 2018, 8 pages.
International Preliminary Report on Patentability received in PCT/US2017/037987, dated Dec. 27, 2018, 11 pages.

\* cited by examiner

SWING ANALYSIS METHOD USING A SWEET SPOT TRAJECTORY

This application is a continuation of U.S. Utility patent application Ser. No. 15/628,613 filed 20 Jun. 2017, issued as U.S. Pat. No. 10,124,230, which is a continuation-in-part of U.S. Utility patent application Ser. No. 15/214,339 filed 19 Jul. 2016, the specifications of which are hereby incorporated herein by reference.

BACKGROUND OF THE INVENTION

Field of the Invention

One or more embodiments setting forth the ideas described throughout this disclosure pertain to the field of motion capture sensors and analysis of motion capture data. More particularly, but not by way of limitation, one or more aspects of the invention enable a method for analysis of a baseball swing using data captured from a motion sensor on the bat.

Description of the Related Art

Methods for analyzing swings of a piece of equipment, such as a golf club, tennis racquet or baseball swings for example include video capture systems that record high speed video of a swing and that analyze the motion of the piece of equipment, club, racquet or bat, etc., and the player from the video. These systems are typically expensive and complex, and they are not portable. Another method is to attach a motion sensor to the piece of equipment, e.g., a bat, etc., and to analyze motion data captured by the sensor during the swing. A significant challenge for these sensor based solutions is interpretation of the sensor data. In particular, sensors typically capture data in a local reference frame defined by the sensor geometry. This sensor reference frame moves and rotates constantly throughout a swing. For example, for a baseball bat, this challenge is more complex since the bat has rotational symmetry around its long axis; thus the batter can hold the bat in multiple orientations while swinging, which changes the sensor data. This applies to other sports that involve a swing of a piece of equipment and any discussion oriented towards a bat herein is not limiting, and can be applied to any other type of equipment that involves a swing as well. There are no known methods that transform swing sensor data from a sensor based reference frame to a meaningful reference frame that is insensitive to these changes in orientation. Existing methods emphasize vector magnitudes (such as total swing speed) in defining swing metrics because these magnitudes are invariant to rotations in the sensor reference frame. However, individual components of sensor measurements along carefully chosen transformed axes provide more detailed and more physically meaningful information.

In baseball and related sports, the trajectory of specific point on the bat or other piece of equipment, for example the sweet spot, is of particular importance since this is the optimum location on the bat for striking the ball. There are no known methods that combine analysis of the sweet spot trajectory with a swing plane reference frame.

For at least the limitations described above there is a need for a swing analysis method using a sweet spot trajectory.

BRIEF SUMMARY OF THE INVENTION

Embodiments of the invention enable a method to analyze a swing of a piece of equipment, for example a baseball bat, tennis racquet, or golf club, etc., by transforming sensor data captured during the swing to a reference frame that reflects the physics and geometry of the swing itself. This reference frame is called a swing plane reference frame. Metrics defined with respect to the swing plane reference frame provide a detailed characterization of a swing; these metrics can be compared across swings to analyze the factors that affect swing performance. For simplicity, examples directed at baseball bat swings are detailed herein, however, the exemplary embodiments described herein may also be applied to any other piece of equipment that involves a swing, including but not limited to a golf club, tennis racquet, etc.

One or more embodiments of the invention may obtain sensor data from a sensor coupled to a bat while the bat is swung to hit or otherwise contact a ball. The bat may be for example, without limitation, a baseball bat, a softball bat, or a cricket bat. The sensor may for example be an inertial motion sensor that includes any or all of a three axis accelerometer, a three axis gyroscope, and a three axis magnetometer. The sensor may be a compound sensor that incorporates multiple individual sensors of any types. A compound sensor may include multiple sensors at different locations on the bat; for example, without limitation, some sensors may be located on the knob of the bat, and other sensors may be located at the tip of the bat. Sensor data may be collected throughout the swing, for example at a rate of 10 Hz, 100 Hz, 1000 Hz, or more. The sensor data may be analyzed to determine the time of impact between the bat and a ball. For example, accelerometer data, i.e., or acceleration data, may detect the shock of the impact. A bat trajectory may be calculated from the sensor data. The trajectory may include motion data samples at multiple points in time throughout the swing; each motion data sample may describe one or more of the bat's position, orientation, velocity, angular velocity, acceleration, or angular acceleration at a point in time.

Analysis of the bat trajectory may include calculating an impact velocity vector for the velocity of the bat at the time of impact with the ball. Using the impact velocity vector, a reference frame called the swing plane reference frame may be defined for the swing. The swing plane reference frame may be formed from three axes: a first axis may be the longitudinal axis of the bat; a second axis may be the impact velocity vector; and a third axis may be orthogonal to the swing plane spanned by the first (bat) axis and the second (impact velocity) axis. The angular velocity vector of the bat, which is the rotational axis that is perpendicular to the bat's instantaneous plane of rotation, may also be used to define or calculate one or more of the axes of the swing plane reference frame. The bat trajectory may then be transformed to the swing plane reference frame for further analysis. This analysis may include creating one or more swing metrics from the transformed bat trajectory.

Illustrative metrics that may be defined using the transformed bat trajectory include the following: Swing plane speed at any point in time during the swing may be defined as an instantaneous rotational speed of the bat trajectory projected onto the swing plane. In one or more embodiments, this swing plane speed may be calculated by projecting angular velocity onto the normal vector of the swing plane. Swing duration may then be calculated by defining the start of downswing as the latest time prior to impact when the swing plane speed has magnitude zero. Subtracting the start of downswing from the time of impact generates a duration metric called the time to contact, which measures how quickly the batter responds. The amount of bat motion may be measured as the total angle traversed by the bat both in the swing plane (yielding a metric called total swing angle) and in a plane orthogonal to the swing plane (yielding a different metric called off plane angle). A measure of bat acceleration through the swing may be defined by measuring the swing plane speed at the halfway point of a swing; the ratio of this halfway point swing plane speed to the peak swing plane speed through the swing is defined as the swing tempo metric.

One or more embodiments may obtain a database of swings from multiple players. Analysis of the database may be used to generate one or more performance rating functions that rate swings on their relative performance. These performance rating functions may be applied to rate future swings, and to provide feedback to users on the performance and characteristics of their swings. Metrics and other data associated with swings in the database may be combined into feature vectors that may be used for classification and matching algorithms. For example, analysis of the database may be used to group swings into swing styles, where swings associated with the same swing style have similar feature vectors. Feature vector clustering and matching may be used to provide feedback to a user on the style of his or her swing, and to identify other users with similar swings. The feature vector may also include other data related to the swing event, such as for example incoming pitch trajectory or classification, outgoing ball trajectory, or game outcome (such as foul, fly-out, home run, etc.) in order to refine classification and analysis.

In situations where sensor data is unavailable or is saturated at the limit of the sensor's range for a time interval during a swing, one or more embodiments may extrapolate sensor data prior to or after the interval to estimate actual values during this interval. Extrapolation may for example use a Bezier curve. The curve may be for example a cubic Bezier curve with four control points that are selected to match the values and the slopes of the sensor data curve at the endpoints of the interval. One or more embodiments may use a Kalman filter, or a similar state space estimator, to extrapolate sensor data into the time interval. A Kalman filter may for example incorporate a kinematic model of the bat in order to predict motion parameters when sensor readings are not able to fully track the motion, for example because the motion is outside the sensor's measurement range.

One or more embodiments of the invention may calculate a trajectory of the sweet spot or of a similar or other point on a bat or piece of equipment, and may derive metrics describing a swing from this trajectory. The sweet spot trajectory may be calculated from sensor data, for example from a sensor coupled to the bat, which may for example include accelerometer or gyroscope data. Data may be transformed to a reference frame that may for example be centered at the sweet spot at the time of impact. A reference frame may be defined for example, without limitation, with a z-axis pointing vertically upward, and an x-axis oriented so that the longitudinal axis of the bat is in the xz-plane at impact. The time of impact may be calculated by searching the sensor data time series for event signatures that may for example have acceleration and angular velocity exceeding respective threshold values. A sweet spot as utilized herein may also indicate a range of location or shape of area on the piece of equipment where an impact occurs or is to occur, wherein the sweet spot meets a predefined threshold, or value, for maximum energy transfer, maximum ball speed or least vibration or any other metric related to efficiency or power for example, or using any other metric to define the location or range or area or area range on the piece of equipment.

One or more embodiments may detect a virtual impact for an air swing, when a bat may not physically strike a ball. For example, one or more embodiments may detect an air swing by determining whether the swing is a valid air swing, and then detecting a point in the swing when angular velocity in the xy-plane is maximum. A valid air swing may for example require that peak xy angular velocity and peak z-axis acceleration exceed respective threshold values.

One or more embodiments may calculate a start of downswing for a swing, and may calculate a time to contact metric as a difference between the time of impact and the start of downswing.

One or more embodiments may calculate the trajectory of the position of the hands on the bat through the swing. This trajectory may be used for example to calculate a center of rotation for the swing. For example, the center of rotation may be calculated as a point equidistant from the hand position at three different points on the hand trajectory. An axis of rotation may be calculated as an axis perpendicular to the plane through these three points. A body tilt angle may be calculated as the angle between the axis of rotation and the vertical direction.

One or more embodiments may calculate and use a two-lever model of the swing, which models the swing mechanics as a body lever extending from the center of rotation to the hand position, and a bat lever that extends from the hand position to the sweet spot. A body ratio metric may be calculated based on the ratio of the rotation of the body lever through the swing to the rotation of the bat lever. The angle between the bat lever and the body lever changes through the swing as the batter cocks and then releases the wrist. A hinge angle may be calculated through the swing based on the relative orientation between the bat lever and the body lever; for example, the hinge angle may be defined as the angle between the bat lever and the tangent to the body lever. The hinge angle at impact may be used as a swing metric.

A commit event may be calculated to reflect when the batter releases the wrist during the swing. For example, the time of commit may be calculated as the time when the angular velocity of the hinge angle exceeds a threshold value. The hinge angle at the time of commit may be used as a swing metric. The hinge release metric may be calculated as the difference between the hinge angle at impact and the hinge angle at commit.

One or more embodiments may determine a swing plane for the swing. The swing plane may be calculated based on the position, orientation, and velocity of the bat at the time of impact. For example, the swing plane may be a plane through the sweet spot at impact, which is spanned by the bat's longitudinal axis at impact and by the velocity vector of the sweet spot at impact.

At any point in the swing, the distance between the sweet spot and the swing plane may be calculated as an off-plane distance. An on-plane event may be calculated as the point in the swing when the off-plane distance is within a specified threshold and remains within this threshold until impact. An on-plane metric may be calculated as the angular range of motion of the bat or of one or both of the body and bat levers between the on-plane event and the impact event.

The bat forward velocity at any point in time may be calculated as the velocity of the sweet spot projected onto a plane perpendicular to the longitudinal axis of the bat. Bat speed at impact may be calculated as the forward bat speed at the time of impact. A peak bat speed may be calculated as the maximum forward bat speed through the swing. Swing power may be calculated as a product of the bat speed at impact, the mass of the bat, and the average acceleration of the sweet spot during the swing.

A swing plane tilt angle metric may be calculated as the angle between the bat's longitudinal axis at impact and the horizontal. An attack angle metric may be calculated as the angle between the sweet spot velocity vector at impact and the horizontal.

One or more embodiments of the invention may include utilizing sound or at least one Virtual Reality (VR), Augmented Reality (AR) or Mixed Reality (MR) display, glasses or goggles to provide bio-feedback to the user. For example, in one or more embodiments, a sound or visual display may be utilized to provide feedback to the user to indicate a correct position, or movement has been achieved. This enables a user to work on portions of a swing or an entire swing using different body positions, for example to simulate different feet positions in a sand trap for a golf swing for example and obtain feedback regarding the position and/or swing using sound or visual feedback. In addition, by providing metrics regarding the body position, body movement, piece of equipment position, piece of equipment movement or any combination thereof, embodiments of the invention enable a user to work on developing more power and improving skills in a bio-feedback environment and/or combine environment. Embodiments of the system also enable rehabilitation and general training of the body based on the data gathered by the system to suggest areas of the body to strength or stretch to improve the range of motion to avoid injury through use of correct biomechanics.

BRIEF DESCRIPTION OF THE DRAWINGS

The above and other aspects, features and advantages of the ideas conveyed through this disclosure will be more apparent from the following more particular description thereof, presented in conjunction with the following drawings wherein.

DETAILED DESCRIPTION OF THE INVENTION

A baseball swing analysis method using a sweet spot trajectory will now be described. In the following exemplary description numerous specific details are set forth in order to provide a more thorough understanding of the ideas described throughout this specification. It will be apparent, however, to an artisan of ordinary skill that embodiments of ideas described herein may be practiced without incorporating all aspects of the specific details described herein. In other instances, specific aspects well known to those of ordinary skill in the art have not been described in detail so as not to obscure the disclosure. Readers should note that although examples of the innovative concepts are set forth throughout this disclosure, the claims, and the full scope of any equivalents, are what define the invention.

Figure 1:
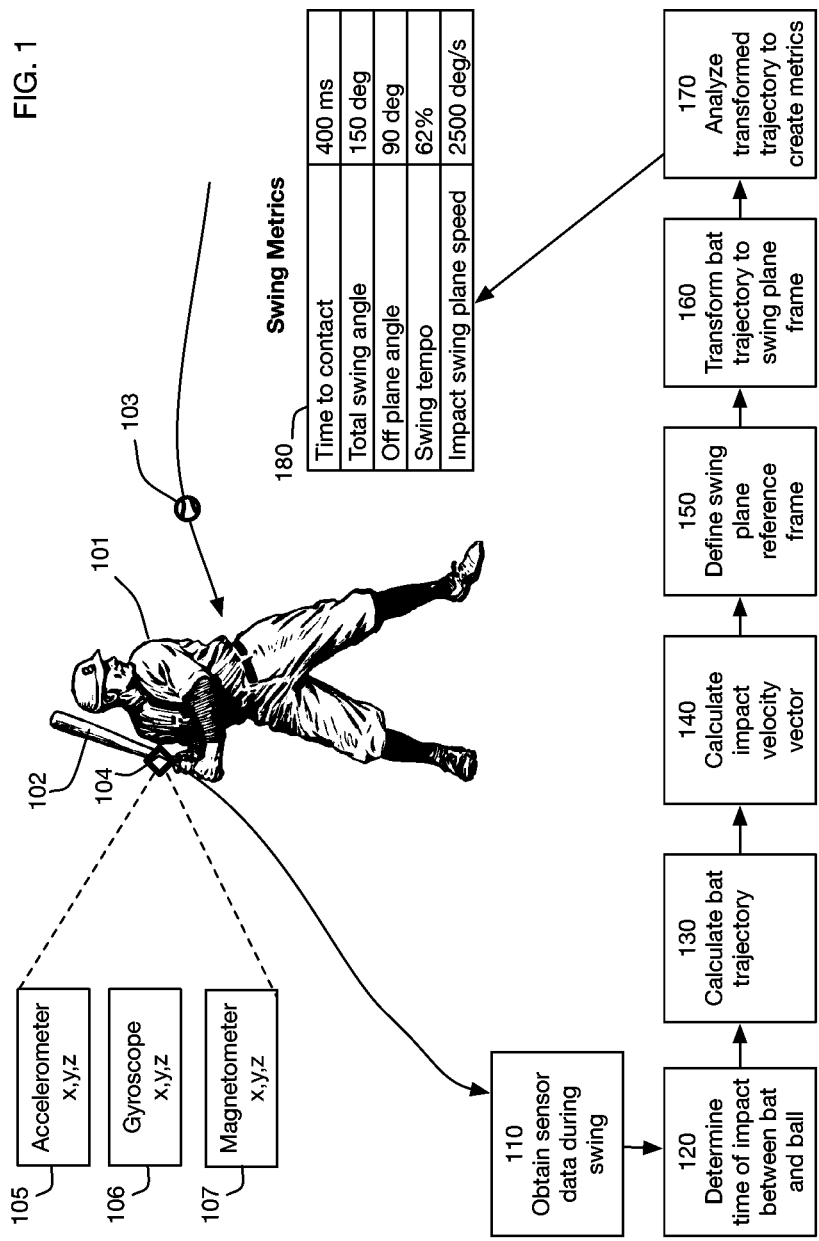
FIG. 1 shows an overview flowchart of an embodiment that processes sensor data in a swing plane reference frame to generate several swing metrics for the swing of a baseball bat.

FIG. 1 shows an overview of an embodiment of the invention. User 101 swings a baseball bat 102 to hit an incoming ball 103. Data is collected throughout the swing from sensor 104 attached to the bat. Sensor 104 may incorporate any type of sensor technology or technologies to measure any quantities, such as for example any aspects of the motion, position, or orientation of the bat. The sensor may be coupled with the proximal end of the bat, the distal end of the bat or anywhere in between. In one or more embodiments the sensor 104 may comprise two or more sensors at different locations on the bat. For example, without limitation, sensor 104 may contain any or all of a three axis accelerometer 105, a three axis gyroscope 106, and a three axis magnetometer 107. These sensor types are illustrative; one or more embodiments may use sensor data from any type or types of sensors to track the swing of bat 102. In one or more embodiments the sensor 104 may not be physically attached to the bat; for example, the sensor may be stationary and it may observe the moving bat using technologies such as video, radar, LIDAR, or ultrasound. In one or more embodiments, data from multiple types of sensors may be combined using sensor fusion. For example, sensor data from an inertial sensor on a bat may be fused with radar data or other information from external devices to calculate a bat trajectory. Sensors may measure motion or other parameters on any number of axes. Sensors may measure these parameters at any desired frequency; higher measurement frequency may for example support more detailed analysis of the swing. For example, without limitation, sensor 104 may collect data once per second, ten times per second, one hundred times per second, one thousand times per second, ten thousand times per second, or at frequencies above ten thousand times per second.

In the embodiment shown in FIG. 1, bat 102 is a baseball bat. One or more embodiments may obtain and analyze data for the swing of any type of bat or similar object, including for example, without limitation, a baseball bat, a softball bat, a cricket bat, and in one or more embodiments, a tennis racket, a table tennis racket, a badminton racket, a squash racket, a racquetball racket, a golf club, a polo mallet, a hockey stick, a field hockey stick, and a lacrosse stick or any other type of equipment that involves a swing.

Data from sensor 104 is obtained in step 110. One or more embodiments may use any data transfer technology or technologies to obtain sensor data. For example, without limitation, data may be transferred over a wireless network, over a wired network, or using a data storage medium that is moved from one system to another. Data may be obtained in real time during a swing, obtained after a swing occurs, or obtained using a combination of real-time transfer and transfer after a swing event.

Steps 120 through 170 analyze data from sensor 104 to characterize the swing, resulting in swing metrics 180. These steps may be performed in any order, or in parallel. These steps may be performed on any system or combination of systems. For example, without limitation, any or all of these steps may be performed on a computer, a mobile computer, a laptop computer, a notebook computer a desktop computer, a tablet computer, a mobile phone, a smart phone, a smart watch, a microprocessor, a server, or a network of any of these devices. In one or more embodiments the sensor 104 may contain a processor or processors that perform some or all of the steps 110 through 170.

Step 120 determines the time of impact between bat 102 and ball 103. This step may for example detect a signature in the sensor data that indicates a collision. For example, if sensor 104 includes an accelerometer such as accelerometer 105, a rapid spike in acceleration may be a signature of an impact. Similarly, if sensor 104 includes a gyroscope such as gyroscope 106, a rapid reduction in angular velocity may be a signature of an impact. One or more embodiments may for example use sensors that directly measure impact, such as pressure sensors or contact switches. In one or more embodiments, a swing endpoint may be defined even if the bat does not hit the ball, for example during practice swings, air swings, or strikes. This swing endpoint may be based for example, without limitation, on parameters such as the location of the bat relative to the plate or to an incoming ball, the aim angle of the bat, or the point in time when the bat achieves maximum velocity or maximum angular velocity. A calculated swing endpoint may be used instead of an actual impact time for any of the subsequent metric calculations described below.

Step 130 calculates a trajectory of the bat 102 from a starting point of the swing through the impact time determined in step 120. In one or more embodiments the trajectory may also extend beyond the impact or prior to the start of the swing. The bat trajectory may be a time series of motion data samples, each of which represents the state of the bat at a point in time during the swing. For example, each sample may include data on any or all of the bat's position, orientation, velocity, angular velocity, acceleration, or angular acceleration. In one or more embodiments a sample may include data for multiple locations on the bat. Methods to calculate an object's trajectory from motion sensor data are known in the art. For example, one or more embodiments may use inertial navigation algorithms known in the art to calculate the position and orientation of the bat over time from acceleration data (for example from accelerometer 105) and from angular velocity data (for example from gyroscope 106). Data from other sensors, such as for example magnetometer 107, may for example provide redundant measurements to correct errors in inertial navigation algorithms.

Because the orientation and position of sensor 104 changes throughout the swing, the bat trajectory calculated in step 130 may not be in a convenient form for analysis. Therefore, in step 150 a standardized reference frame is defined based on the swing itself. We refer to this reference frame as the swing plane reference frame. In step 160 the bat trajectory is transformed to this reference frame. In step 170 the transformed trajectory is used to analyze the swing, and to generate one or more swing metrics describing and characterizing the swing. Illustrative swing metrics 180 describe for example the timing of the swing, the speed of the swing, and the angles traversed during the swing.

Figure 2:
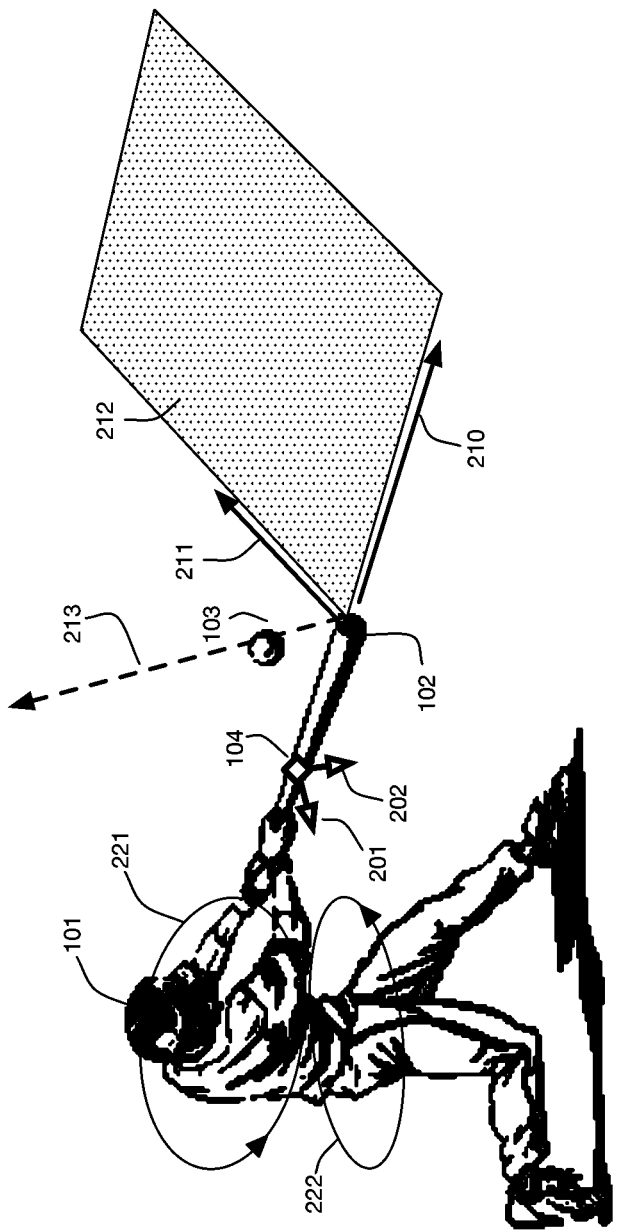
FIG. 2 shows a reference frame based on a swing plane defined by the bat orientation and by the velocity vector of the bat at the time of impact with the ball.

FIG. 2 illustrates definition and calculating of the swing plane reference frame. This reference frame is defined by the bat's orientation and motion at the time of impact between the bat 102 and the ball 103. A swing plane 212 is defined by two axes: a first axis 210 is the longitudinal axis of the bat (along the bat's long dimension); a second axis 211 is in the direction of the bat's velocity at the time of impact. The velocity vector at impact may also be calculated as a tangent vector to the bat's instantaneous rotation round the angular velocity axis. This impact velocity vector 211 may be calculated or obtained from the bat trajectory. In one or more embodiments a specific point on the bat, such as for example the sweet spot, may be used to define the impact velocity vector. The swing plane 212 is the plane spanned by the vectors 210 and 211. To complete the reference frame, a third orthogonal off-plane axis 213 is selected as the normal vector to the plane 212. The swing plane 212 defined by the axes 210 and 211 provides a reference frame that can be calculated from data generated by bat sensor 104. Other planes of rotation that may be relevant to the kinematics of the swing include for example the rotational plane 221 for the batter's shoulders, and the rotational plane 222 for the batter's hips. In one or more embodiments additional sensors, for example sensors attached to the batter's shoulders and hips, may be used to calculate these body rotational planes in addition to the swing plane 212.

Figure 3:
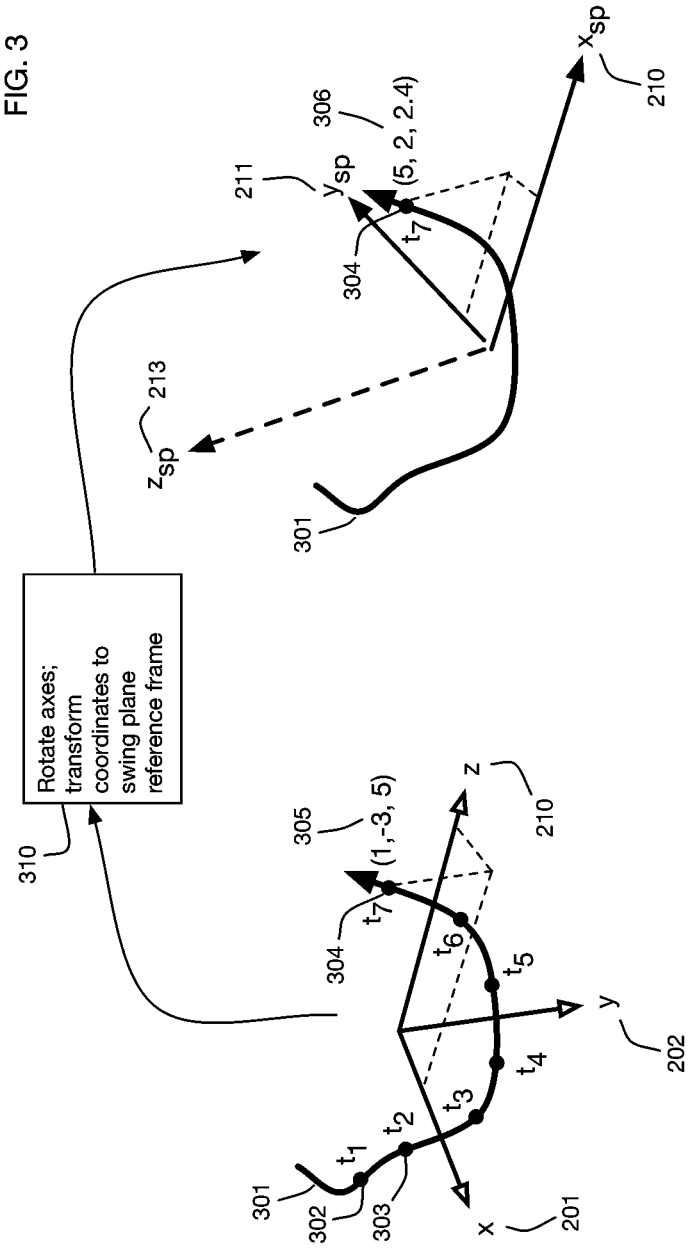
FIG. 3 illustrates transformation of a bat trajectory from a local sensor frame to the swing plane reference frame of FIG. 2.

In the example shown in FIG. 2, sensor 104 has a local reference frame in which sensor data is measured. This local reference frame in general may have a completely different orientation from the swing plane reference frame defined by axes 210, 211, and 213. For example, the sensor local reference frame may have axes 201, 202, and 210; in this example one axis of the sensor local reference frame is aligned with the bat longitudinal axis, but the other axes are in arbitrary directions due to the rotational symmetry of the bat around this axis. To facilitate standardized analysis of swings and comparison of swings across players, bat trajectory information is transformed from the sensor local reference frame into the swing plane reference frame. FIG. 3 illustrates this transformation. Bat trajectory 301 includes motion data samples at various points in time, such as for example points 302, 303, and 304. These samples may include any information on the state of the bat, such as position, orientation, or derivatives of these values like velocity and angular velocity. For illustration, the bat trajectory 301 is shown as a single curve in three dimensional space (for example as a curve of bat position over time); however, in one or more embodiments the bat trajectory may include any data with any number of dimensions. In the sensor local reference frame defined, for illustration, by axes 201, 202, and 210, each sample point has coordinates such as coordinates 305 for point 304. Transformation 310 maps the sample points into the swing plane reference frame, for example using a rotation of the axes 201, 202, and 210 into axes 210, 211, and 213. For example, in the swing plane reference frame, point 304 on the bat trajectory 301 has coordinates 306.

Figure 4:
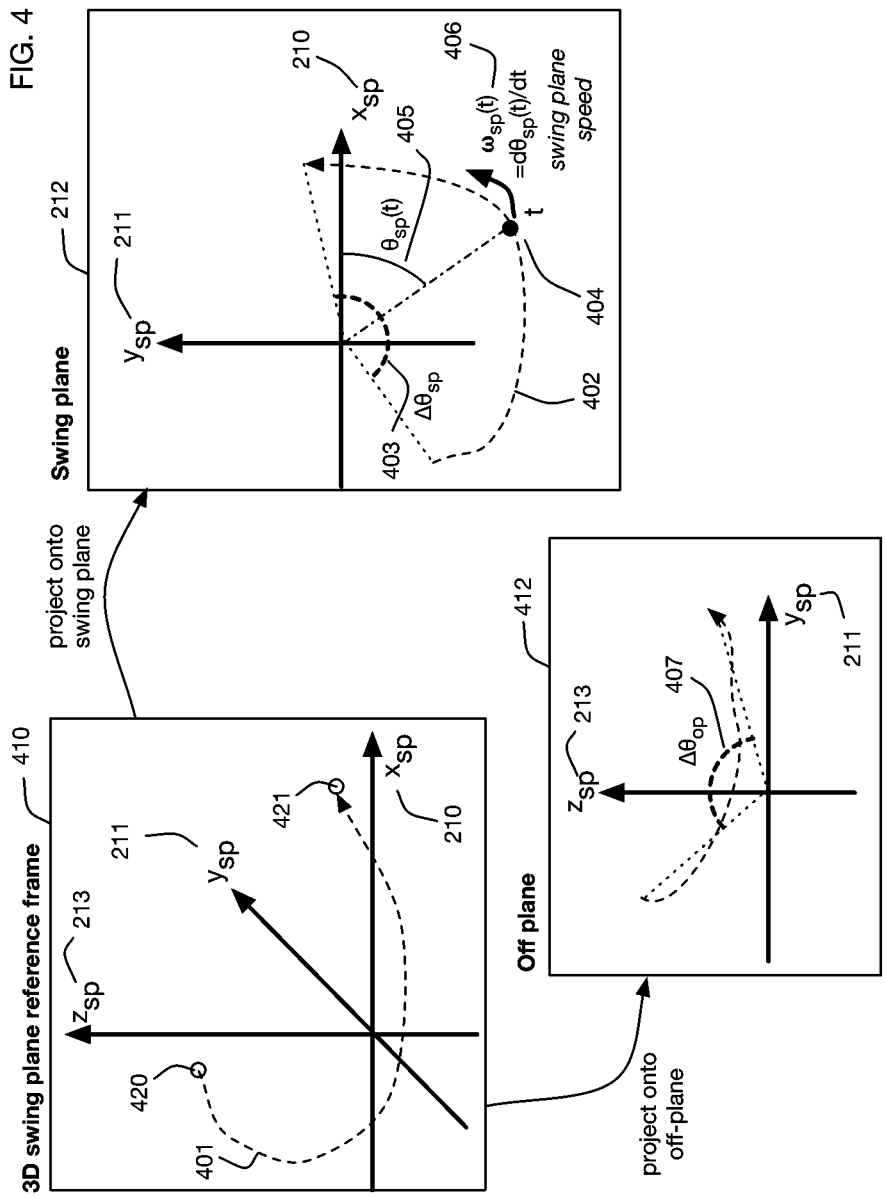
FIG. 4 illustrates various metrics derived from the swing plane reference frame, including a total swing angle in the swing plane, an off-plane swing angle, and a swing plane speed.

One or more embodiments of the invention may analyze the bat trajectory in the swing plane reference frame to measure and characterize the swing. FIG. 4 shows illustrative metrics for angular change that are defined relative to the swing plane reference frame. Bat trajectory 401 is a three dimensional curve in the three dimensional swing plane reference frame 410 defined by axes 210, 211, and 213. Trajectory 401 has starting point 420, representing a start of the swing, and endpoint 421, representing for example the time of impact between the bat and the ball. This curve may be projected onto the two-dimensional swing plane 212 defined by axes 210 and 211, and various metrics may be calculated from this projection. For example, the 2D curve 402 is the projection of the bat trajectory 401 onto plane 212. As the curve 402 proceeds from the starting point to the endpoint of the trajectory, it subtends an angle 403 ($\Delta\theta_{sp}$) in the swing plane (with vertex at the origin). This angle 403, which we refer to as the total swing angle, is a swing metric that indicates the total amount of bat movement during the swing in the swing plane. Similarly, the bat trajectory 401 may be projected onto a plane 412 orthogonal to the swing plane, and the angle 407 subtended by the projected trajectory is a different swing metric that we refer to as the off-plane angle. The total swing angle metric and the off-plane angle metric provide a useful characterization of how the batter is moving the bat through the swing. Projection of the trajectory 401 onto swing plane 212 also provides the measure of the instantaneous angular velocity 406 of the trajectory at any point in time, such as at illustrative point 404. This instantaneous angular velocity in the swing plane, which we refer to as the swing plane speed, is a more useful metric of the bat's motion than for example the total linear velocity of the bat, which includes an off-plane component of velocity that is not as relevant for the power of the swing. The swing plane speed 406 may be calculated for example as the derivative of the instantaneous angle 405 between the point 404 on the projected trajectory 402 and the axis 210. In one or more embodiments that include a gyroscope, which measures angular velocity directly, the swing plane speed may be calculated by projecting the measured angular velocity onto the axis orthogonal to the swing plane 212.

Figure 5:
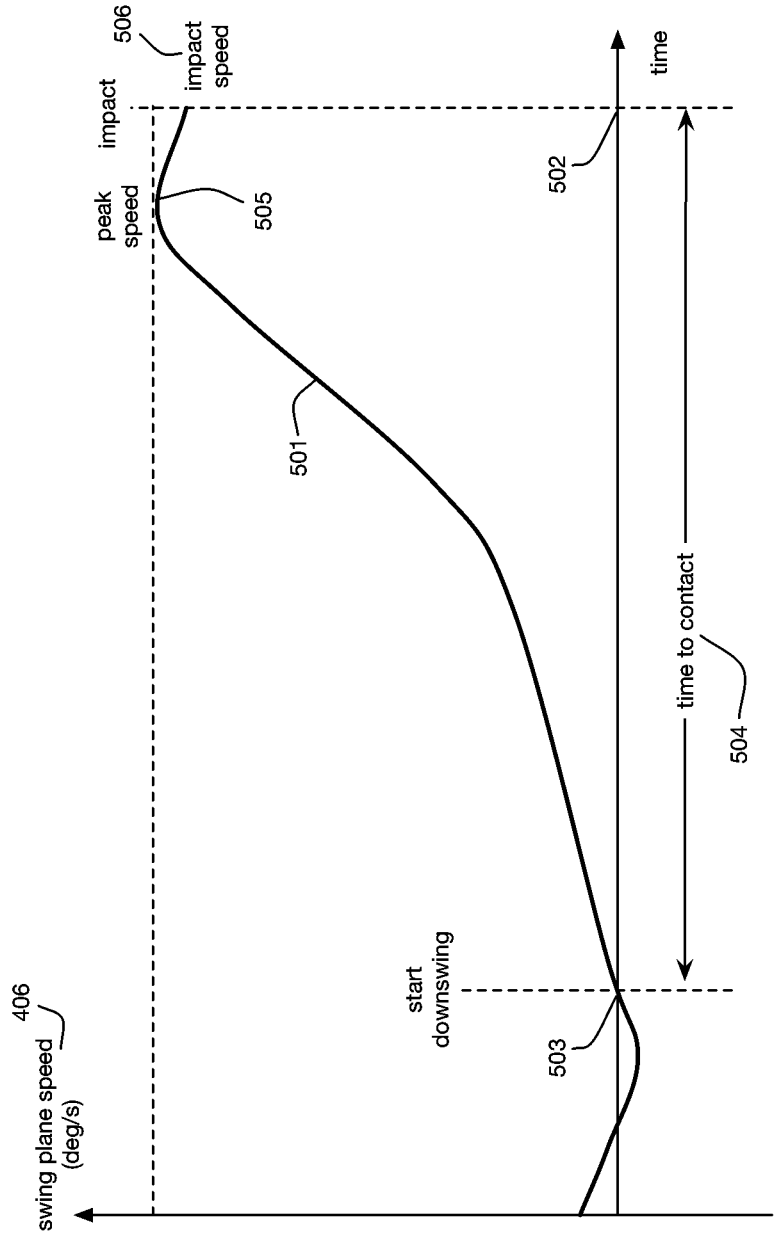
FIG. 5 illustrates derivation of a time to contact swing metric that measures how quickly the batter responds.

The curve of swing plane speed over time through the swing provides additional useful information about the swing. FIG. 5 shows an illustrative curve 501 of the swing plane speed 406 as a function of time. The curve typically increases through the swing as the batter accelerates the bat. The swing plane speed reaches a maximum value 505 during the swing. For some swings, the peak speed 505 may occur at the time of impact 502; however, this is not necessarily the case for all swings. The impact swing plane speed 506 is an important swing metric since it greatly affects the distance and power of the hit. The swing plane speed curve may be used to define an unambiguous point in time for the start of the downswing of a swing: this start of downswing 503 may be defined as the last point in time when the swing plane speed is zero prior to the impact. This definition is based on an unambiguous physical event rather than an arbitrarily defined threshold crossing. This provides a clear advantage in terms of metric consistency and physical significance. If there is no zero crossing, as is the case in certain swing styles, we define the start of downswing where the slope and magnitude of the swing plane component meet certain threshold criteria. This fallback definition does not provide the clear advantages of the zero crossing; however, because it is based on the swing plane component, it provides greater consistency than a definition based on vector magnitude, particularly across heterogeneous swing styles where much of the variability (e.g., bat waggle) occurs in the off-plane component.

Using the start of downswing 503 and the time of impact 502, a total swing time, which we refer to as the time to contact metric, may be defined as the difference 504 between the impact time 502 and the start of downswing time 503. This time to contact metric is an important metric related to the batter's ability to read the pitch.

Figure 6:
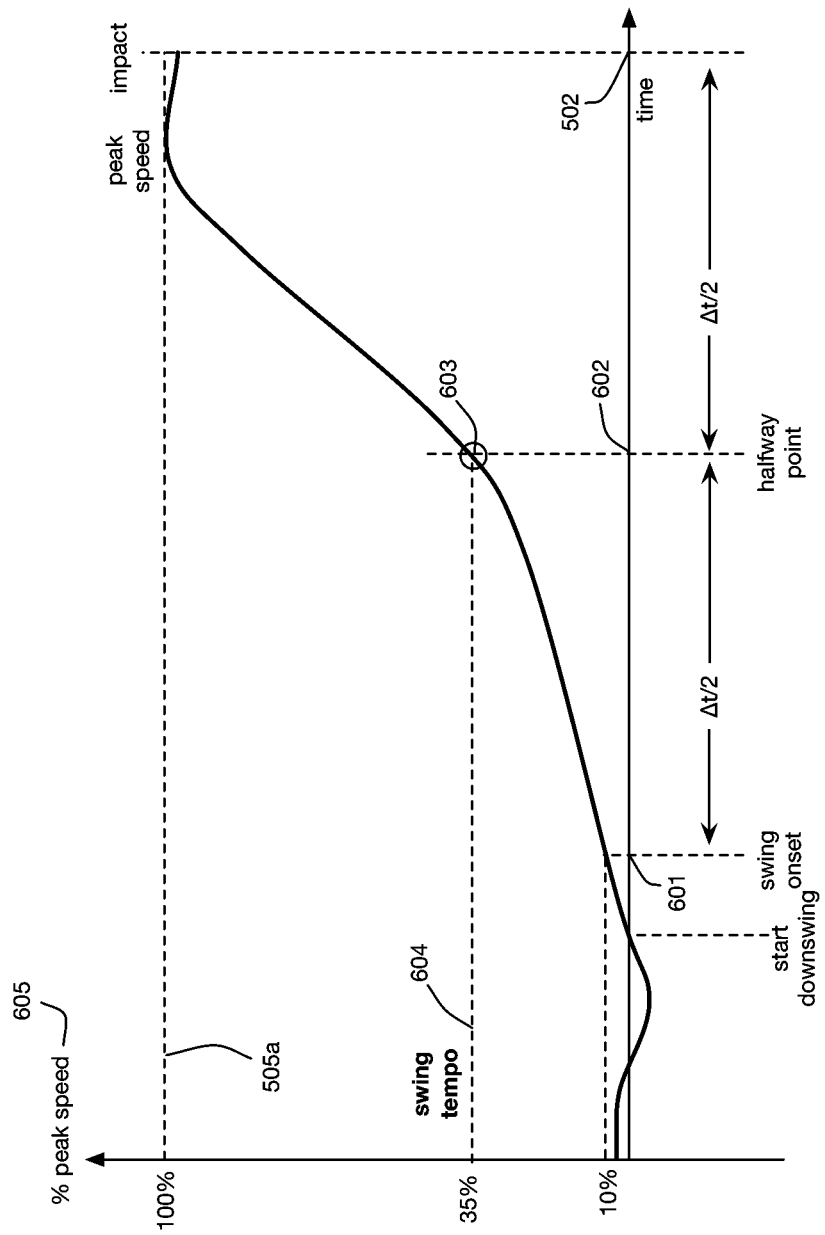
FIG. 6 illustrates derivation of a swing tempo metric based on swing plane speed, which indicates how quickly the swing plane speed increases through the swing.

The rate at which the swing plane speed increases through the swing also provides a useful metric. FIG. 6 illustrates a method to standardize this metric by measuring the fraction of the peak speed achieved at the halfway point of the swing. To allow meaningful comparison across players with different swing styles, the swing plane speed curve is normalized so that swing plane speed is measured as a percentage 605 of the peak speed. Thus the normalized swing speed curve starts at zero at the start of downswing, and increases to 100% at the peak speed. A halfway point 602 is defined for the swing, and the fraction 603 of the peak speed at this point is defined as the swing tempo metric 604. In one or more embodiments the halfway point may be defined as halfway between the start of downswing and the time of impact. However, empirical analysis of swings shows that a more robust halfway point may be defined by selecting a swing onset time 601 as a time at which the swing plane speed reaches a specified small fraction of the peak speed, such as for example 10%, and by defining the halfway point as halfway between the swing onset time and the time of impact.

This definition of the swing tempo metric is based on the insight from comparing statistical distributions, where the greatest variability in deviation from an ideal curve occurs at the half-way point between two fixed endpoints. The significance of this metric comes from an understanding of the kinematic chain (hips, shoulders, arms, wrists) for transferring energy from the body to a baseball bat. A rotationally efficient swing will derive a certain amount of energy from the hips and shoulders compared to the arms and wrists. We can infer how rotationally efficient a baseball swing is by the percentage of speed in the "body" half of the swing relative to the "arm" half. An ideal swing tempo range is learned from empirical data collected from elite-level batters. Deviation from the ideal tempo range, either high or low, is used to provide feedback and prescribe drills to the batter in order to improve performance. A low tempo typically indicates that the swing is dominated by arms (e.g., casting), while a high tempo indicates that a swing is dominated by body (at the expense of bat control).

In one or more embodiments, additional tempo metrics may be defined at other points in a swing, in addition to the halfway point tempo metric described above. For example, without limitation, an early tempo metric may be defined as the fraction of peak speed achieved at the 25% point of the swing, a mid-tempo metric may be defined as the fraction of peak speed achieved at the 50% point of the swing (as discussed above), and a late tempo metric may be defined as the fraction of peak speed achieved at the 75% point of the swing. The three tempo metrics may isolate the effect of different segments of the kinematic chain of the swing; for example, the early tempo metric may characterize the rotation of hips and torso, the mid-tempo metric may characterize the rotation of the torso and arms, and the late tempo metric may characterize the rotation of the arms and bat. These percentages are illustrative; one or more embodiments may measure swing tempo at any point or points in a swing.

Figure 7:
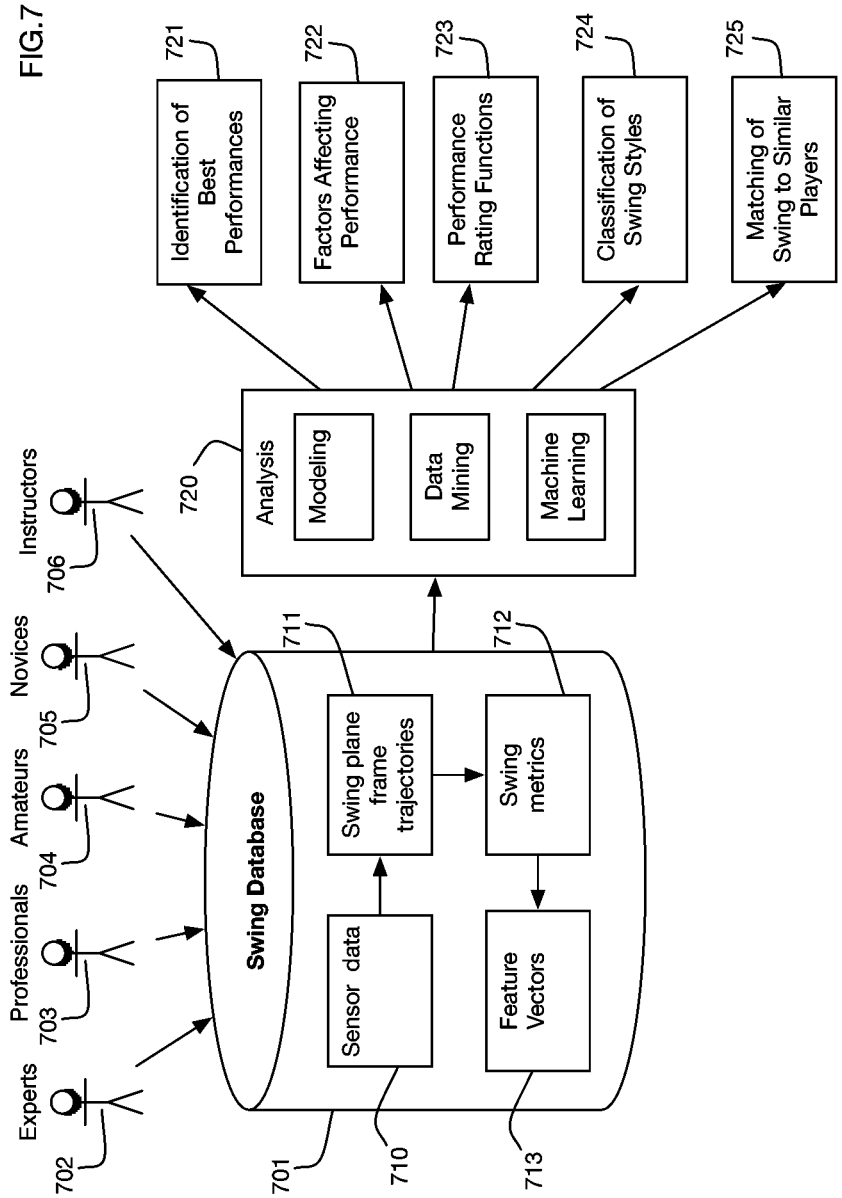
FIG. 7 illustrates an embodiment that collects swing data from multiple users into a swing database, and that analyzes this database to generate methods of rating and classifying swings.

In one or more embodiments, swing data and swing metrics may be collected from multiple users and organized in a swing database for further analysis. FIG. 7 illustrates an embodiment that collects data into swing database 701 from multiple types of users, including for example, without limitation, experts 702, professionals 703, amateurs 704, novices 705, and instructors 706. Data in the swing database may include for example, without limitation, sensor data 710, bat trajectories in the swing plane frame 711, and swing metrics 712 (such as for example the total swing angle, off-plane angle, time to contact, impact swing plane speed, and tempo metrics described above). Multiple metrics may be combined into feature vectors 713 that may be used to classify, categorize, compare, or analyze swings. Data from the database may be used for various analysis procedures 720, which may include for example any or all of modeling swings and batters, data mining the database for patterns or trends, and applying machine learning techniques to learn relationships, functions, or categories. Outputs of the analyses 720 may include for example identification of best performances 721 that flag certain swings or groups of swings as illustrative of ideal or maximum performance; factors affecting performance 722 that identify swing characteristics that contribute to or detract from high performance; performance rating functions 723 that rate swings on how close they are to ideal performance levels; classifications of swing styles 724 that map swings into categories reflecting similar characteristics or similar performance; and matching of swings to similar players 725 that indicate which other swings or other players are most similar to a given swing or player.

Figure 8:
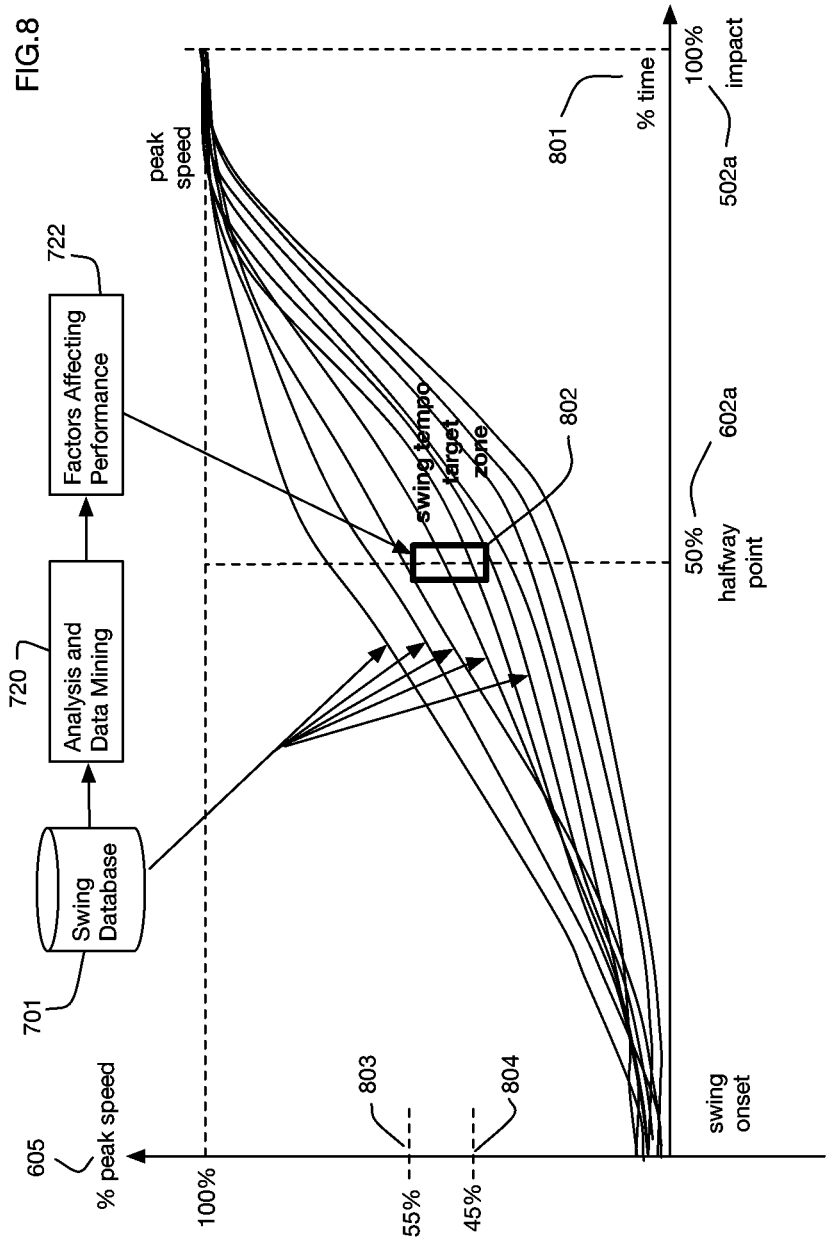
FIG. 8 illustrates an embodiment that analyzes swing tempo from multiple users to determine a target zone for peak performance.

FIG. 8 illustrates an example of the data analysis methods described with respect to FIG. 7, using the swing tempo metric defined above. Using swing database 701 as input, data analysis and data mining process 720 compares swing plane speed curves across players to determine factors affecting performance 722. This analysis indicates that best performance occurs when swing tempo is in a target zone 802, for example in a range between 804 and 803. This analysis uses normalized swing plane speed curves for the swings in database 701, with the swing plane speed axis normalized to the percentage of peak speed 605, and the time axis 801 normalized to a percentage of swing time between swing onset (0%) and impact 502a (100%). The normalized swing plane speed at halfway point 602a (50%) is the swing tempo metric for each swing.

Figure 9:
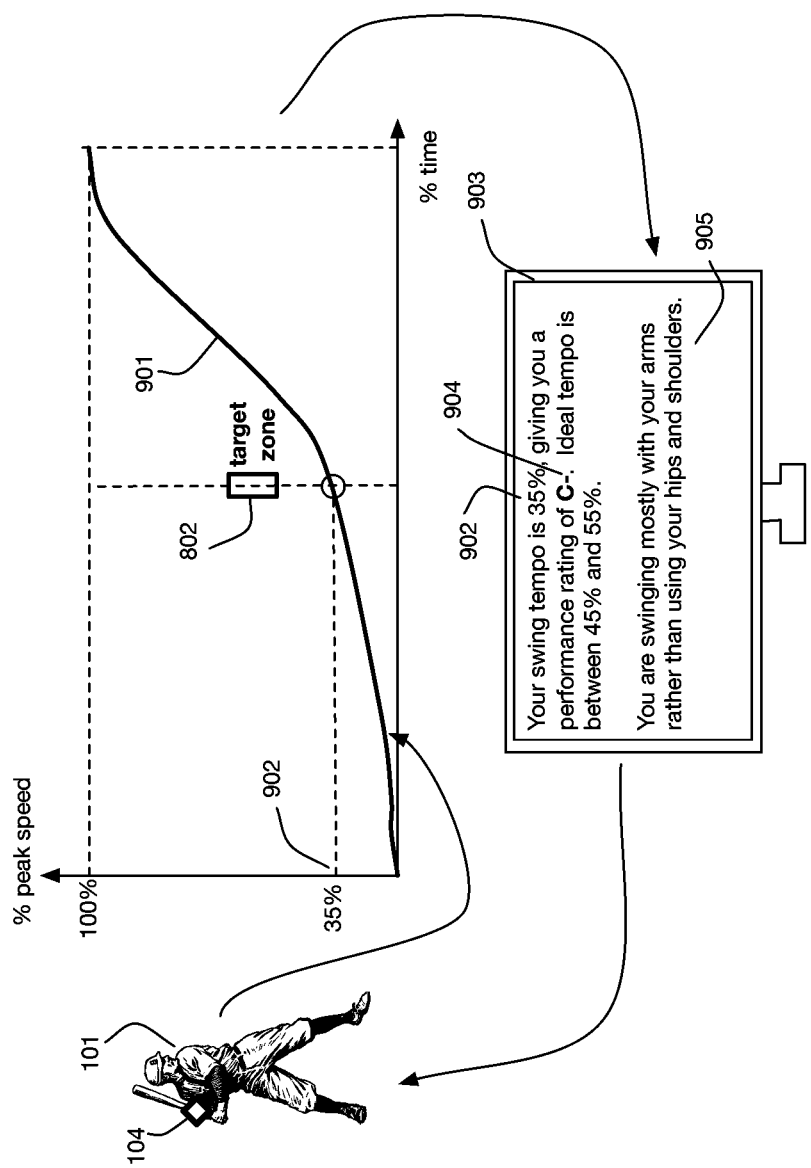
FIG. 9 shows an embodiment that provides feedback to a user on his or her swing by comparing the swing tempo to the target zone described in FIG. 8.

Using the analysis illustrated in FIG. 8, an individual swing may be evaluated by comparing it to the empirically derived criteria for best performance. FIG. 9 illustrates an example with batter 101 generating a swing plane speed curve 901 for a swing. The measured swing tempo 902 for this swing is compared to the target zone 802 in order to rate the swing's performance. Feedback is then provided to batter 101, for example on computer screen 903. This feedback provides the swing tempo metric 902, as well as a performance rating 904 that is based on comparing the swing to performance criteria derived from empirical analysis. The feedback may also include specific critiques such as 905 that diagnose the swing or suggest corrections or improvements.

One or more embodiments may provide feedback to a batter or to other users (such as a coach or trainer) using any desired method or system. For example, without limitation, feedback may be displayed on any computer, laptop, notebook, tablet, mobile phone, smart watch, or wearable device. Feedback may be provided using a specific app, or transmitted via general messaging systems such as email or text messages. Feedback may be audio, visual, haptic, or any combination thereof.

Figure 10:
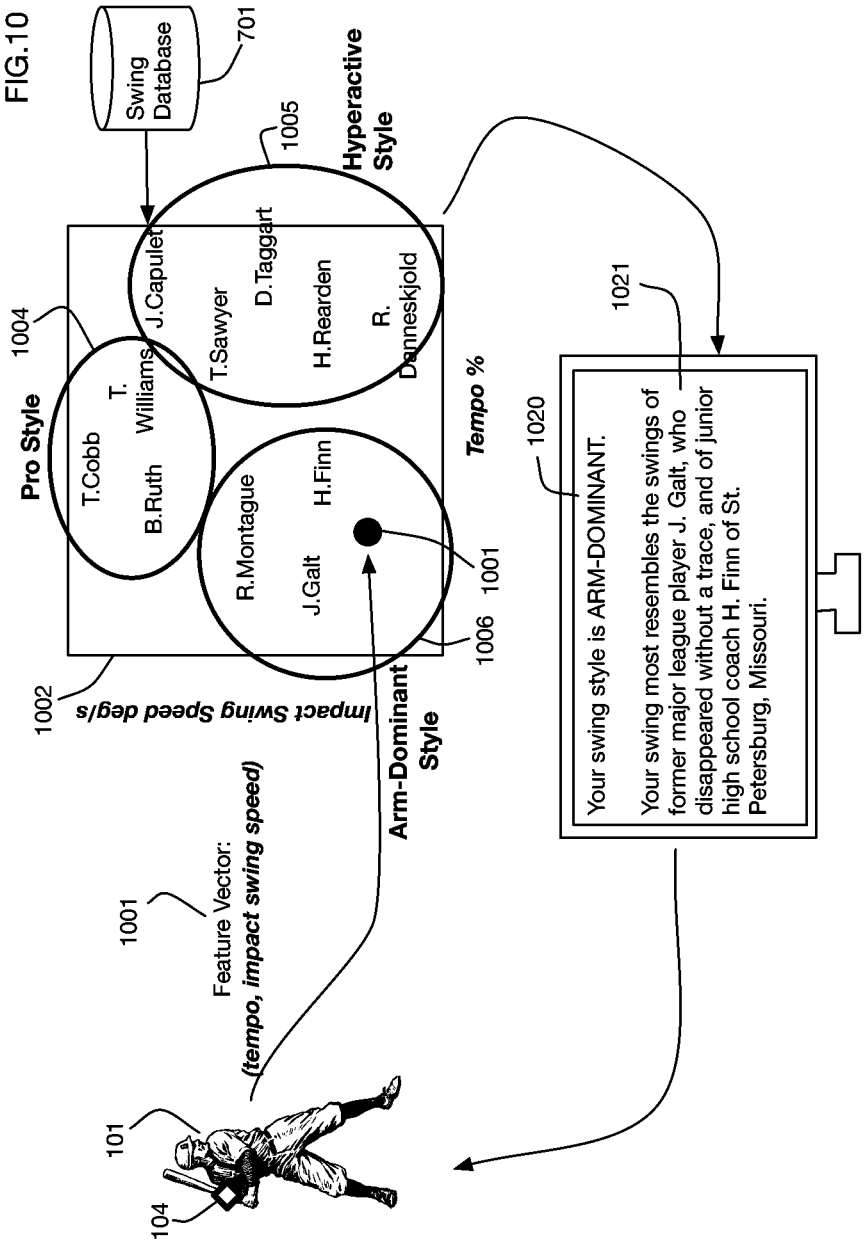
FIG. 10 illustrates an embodiment that classifies swings into swing styles based on a feature vector that combines multiple swing metrics; feedback to a user indicates the swing style as well as identifying other players with similar swings.

FIG. 10 continues the example of FIG. 9 to illustrate additional analysis and feedback for a swing based on comparisons with swings in a swing database. In this example, a feature vector 1001 is generated for a particular swing by batter 101. For illustration, this feature vector is a combination of the swing tempo and the impact swing plane speed. One or more embodiments may generate feature vectors using any combinations of metrics or of any data derived from sensor data or bat trajectories. Swings from swing database 701 are compared on grid 1002 using this feature vector, and are analyzed (for example using cluster analysis techniques known in the art) to categorize swings into a set of swing styles. For example, the analysis may partition swings into three swing styles 1004, 1005, and 1006. The feature vector 1001 corresponding to the swing by batter 101 places the swing into swing style cluster 1006. Feedback to the batter indicates this swing style 1020. In addition, the batter's swing may be matched against typical swings from other users to provide feedback 1021 that identifies other users with swings that resemble the batter's swing.

Figure 11:
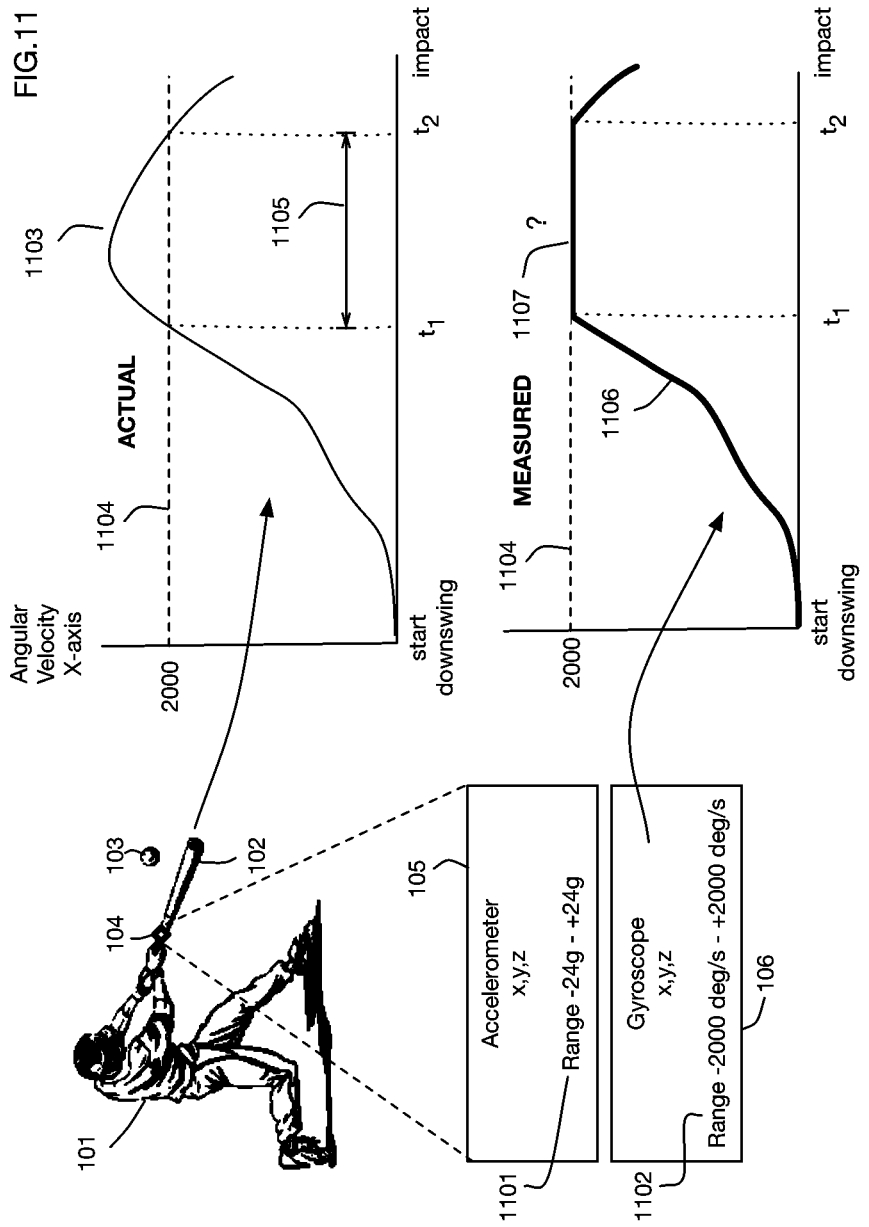
FIG. 11 shows a potential issue that may arise when a sensor has a limited range and the actual motion of the bat exceeds this measurement range during a time interval within the swing.

In some situations, one or more of the sensors that measure the motion the bat may have insufficient range to measure the complete motion throughout the entire swing. FIG. 11 shows an example of this situation where the sensor 104 on bat 102 includes accelerometer 105 with range 1101, and gyroscope 106 with range 106. Taking the angular velocity around the x-axis of the sensor as an illustrative example, the actual x-axis angular velocity 1103 exceeds the upper limit 1104 of measurement range 1102 during time interval 1105. Therefore, the measured sensor values 1106 cannot track the true values 1103 of the motion during this interval 1105. Instead the measured value 1107 during this interval is saturated at the upper limit 1104. This saturation may affect the accuracy of swing metrics. This example using the x-axis of the gyroscope is illustrative; a similar issue may occur with any sensor (including for example the accelerometer 105 as well as the gyroscope 106) and with data from any axis of any sensor.

Figure 12:
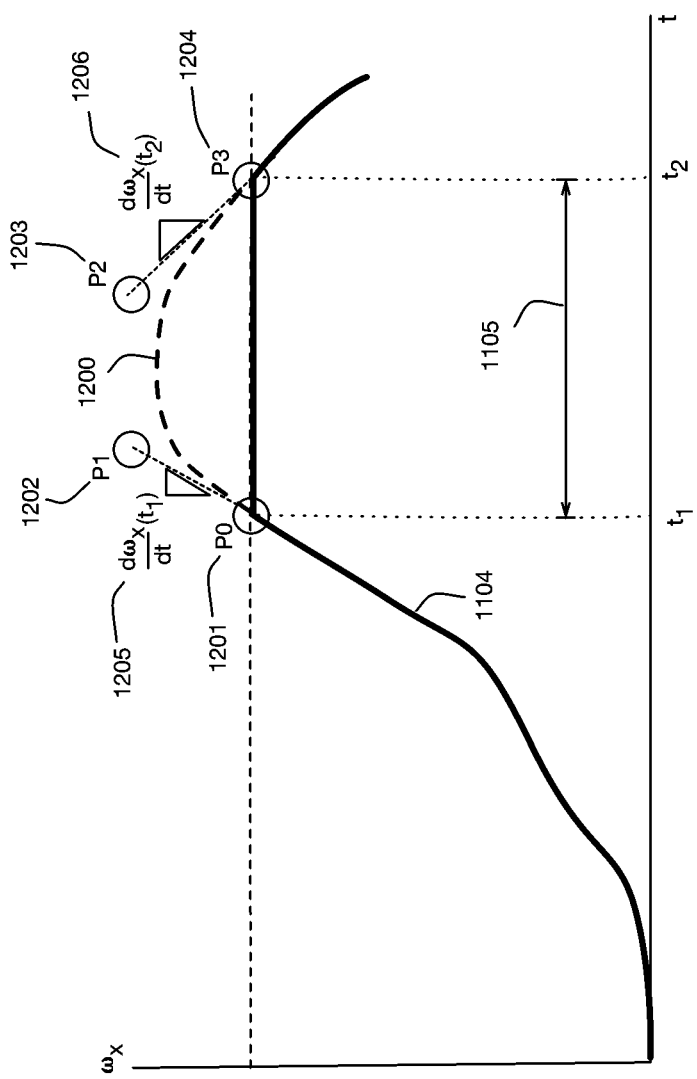
FIG. 12 illustrates an embodiment that addresses the limited range situation shown in FIG. 11 by extrapolating sensor data from before and after the time interval, in this example using a cubic Bézier curve.

To address this issue, one or more embodiments of the invention may extrapolate sensor data from prior to or after the time interval 1105 when the sensor is saturated. Extrapolation may also be used when sensor data is unavailable for a period of time for any other reason, for example because of a limited sampling rate, a recalibration period, or a defective sensor. Extrapolation may be used for any sensor or sensors, or any axis of any sensor or sensors. Embodiments may use any method to extrapolate sensor data into any time interval. FIG. 12 illustrates an embodiment that extrapolates sensor data from both endpoints of the time interval by constructing a Bezier curve 1200 for the values in the interval. In this example, the curve 1200 is a cubic Bezier curve defined by the four control points 1201, 1202, 1203, and 1204. This is illustrative; one or more embodiments may use Bezier curves or any other splines or curves of any order. Control points 1201 and 1204 match the values of the sensor measurements 1104 at the endpoints of interval 1105. The internal control points 1202 and 1203 are chosen to match the slopes of curve 1104 at these endpoints. Specifically, the tangent value 1205 of the curve 1104 at point 1201 is the slope of the line between control points 1201 and 1202, and the tangent value 1206 of the curve 1104 at point 1204 is the slope of the line between control points 1203 and 1204. Points 1202 and 1203 may also be chosen to limit for example the maximum value of the curve 1200 in the interval.

One or more embodiments may select control points for a Bezier curve in such a way as to satisfy the initial and/or final conditions (magnitude and slope) and also to satisfy additional constraints on the maximum absolute value and maximum extrapolation duration. For two-sided extrapolation (no impact events), four control points may be used as shown for example in FIG. 12: the initial and final points are placed where the curve crosses the saturation threshold, and two interior control points are along a line matching the slope of the curve at some distance, which is constrained by some maximum time duration and by a maximum absolute value. This approach provides control of the shape of the extrapolation curve better than a cubic polynomial fit, which will match the same slope and value constraints but may exceed the other physical constraints. If the initial or final edge of the saturation interval is an impact event, then the unconstrained edge may be represented by a single control point, resulting in a three-point Bezier curve. Again, the time and value for this single control point may be selected to achieve the desired shape of the extrapolated curve into the impact event. Because a Bezier curve is not parametric in time, it may be necessary to resample the extrapolated curve at the original sample times. This type of Bezier extrapolation may be applied to an individual saturated sensor axis (independent of the other components) or a composite value (e.g., the x-y resultant or total vector magnitude). The shape of the composite curve may be easier to model or constrain than the underlying individual components for particular kinematic events, resulting in increased accuracy of the extrapolated result. If the underlying component values are needed, they can be obtained by solving for the unknown saturated component(s) from the extrapolated composite result and unsaturated component values (the result will be under-determined if more than one component is saturated).

Figure 13:
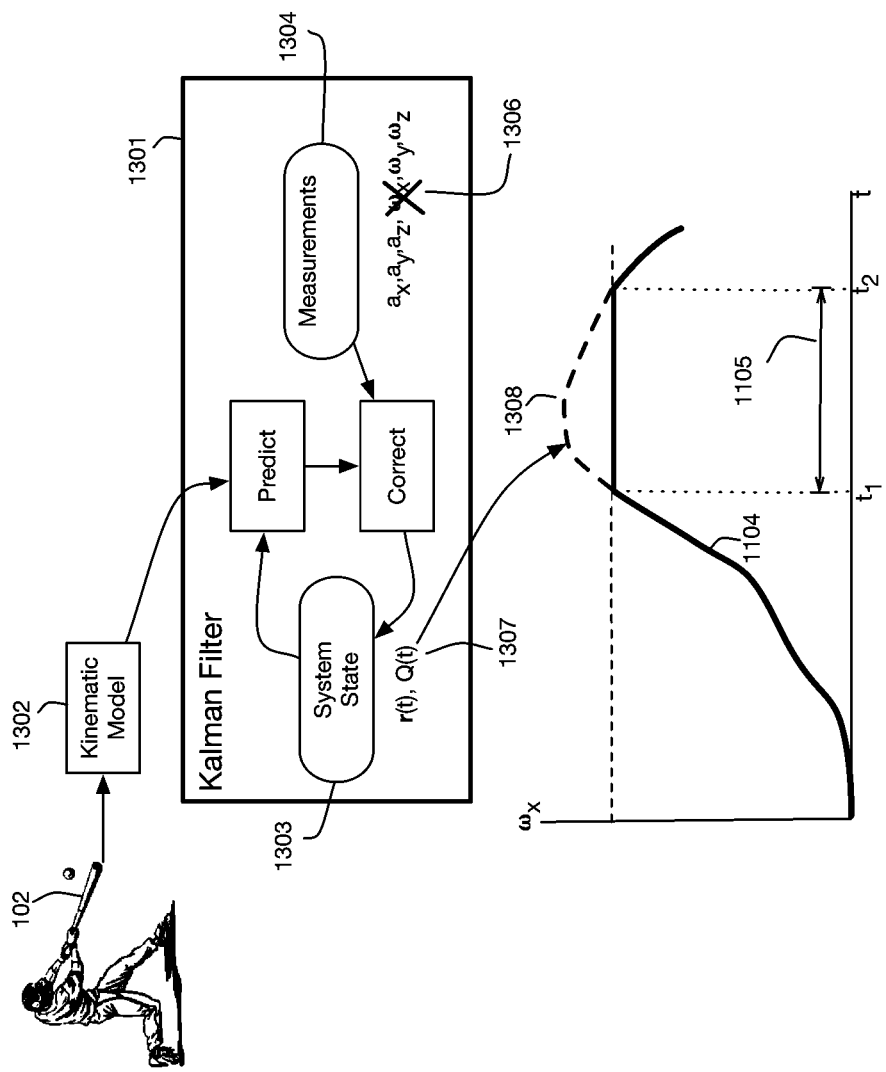
FIG. 13 illustrates an embodiment that extrapolates sensor data using a Kalman filter to estimate values when the measurement range of the sensor is exceeded.

Another approach to extrapolation that may be used in one or more embodiments is to use a Kalman filter (or a variation of a Kalman filter like an Extended Kalman Filter or an Unscented Kalman Filter). FIG. 13 illustrates an example that uses this approach. Kalman filter 1301 incorporates a kinematic model 1302 of the bat 102. The system state 1303 is estimated for each sample point, and this estimate is corrected based on measurements 1304. The state 1303 for example may include the position r(t) and the orientation Q(t) of the bat, and the measurements 1304 may include for example accelerometer values $a_x$, $a_y$, $a_z$ and gyroscope values $\omega_x$, $\omega_y$, $\omega_z$. During time intervals when one or more measurements are not available or are saturated, such as x-axis angular velocity 1306 during time interval 1105, the filter 1301 continues to predict state values 1303. Therefore, the curve 1104 can be extrapolated to curve 1308 through interval 1105; for example, the orientation 1307 may be differentiated to estimate the x-axis angular velocity 1308 in this interval.

In general, one or more embodiments may use a recursive state space estimator (e.g., Kalman filter) with a kinematic model of the physical body or equipment being measured. The state-space propagation model may be used to impose appropriate physical constraints. The state space estimate and its uncertainty (covariance) may be updated using the non-saturated measurements from the various sensors. An estimate of the missing (saturated) parameter may then be derived from the state space estimate. Likewise, the uncertainty in the estimated parameter may be derived from the model uncertainty. Either the state space propagation model or the measurement model (or both) may be non-linear, in which case a linearized (EKF) or sigma-point (UKF) filter may be used. Finally, the uncertainty in the extrapolated time series (or the state space estimate itself) may be propagated to derived metrics. For example, in a baseball swing like the swing illustrated in FIG. 13, the gyroscope may be saturated into impact, which affects the accuracy of the swing speed measurement. Using this approach, it is possible to estimate the actual swing speed and provide an uncertainty interval (error bars).

Figure 14:
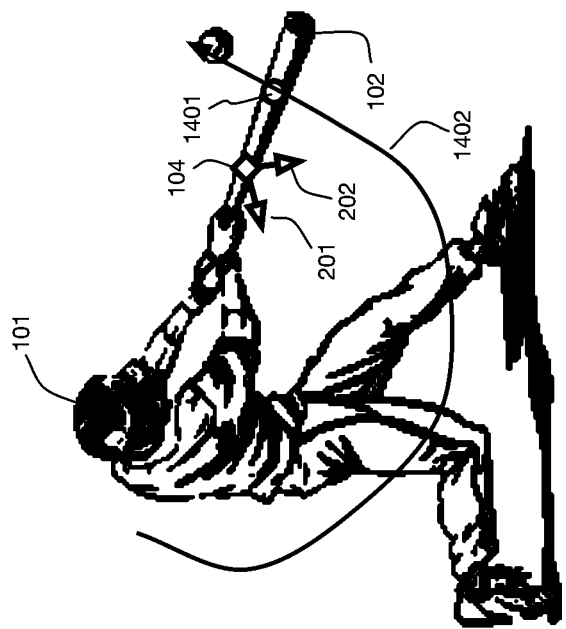
FIG. 14 illustrates an embodiment that tracks the trajectory of the sweet spot of a bat and that calculates swing metrics from this sweet spot trajectory.

In one or more embodiments, a swing of a bat or similar equipment may be decomposed into key events and metrics that provide insight into overall swing quality. Some of these events and metrics may be related to or derived from the trajectory of a sweet spot of the bat. FIG. 14 shows an illustrative swing of bat 102 by batter 101. The bat is equipped with a sensor 104, which may for example include a motion sensor with an accelerometer and a gyroscope. One or more embodiments may obtain sensor data from sensor or sensors 104, and may use this sensor data to calculate the trajectory 1402 over time of sweet spot 1401 of the bat through all or a portion of the swing. The sweet spot location on a bat may be determined by any desired method. For example, several common definitions for the sweet spot of the bat are that it produces the maximum energy transfer to the ball, that it produces the maximum batted ball speed, or that it results in the least vibrational sensation (sting) in the player's hands. These results are not always produced by the same spot on a bat. In addition, the spot may vary based on bat type (wood or aluminum), weight, shape, and other factors. For a more in-depth discussion of the definition, size, and location of the sweet spot for different bat types, see for example Daniel A. Russel, "Physics and Acoustics of Baseball and Softball Bats."

In one or more embodiments, an illustrative definition of a sweet spot may be a location somewhere between four and eight inches from the tip of the bat, such as for example a single point on the centerline of the bat six inches from the tip.

Figure 15:
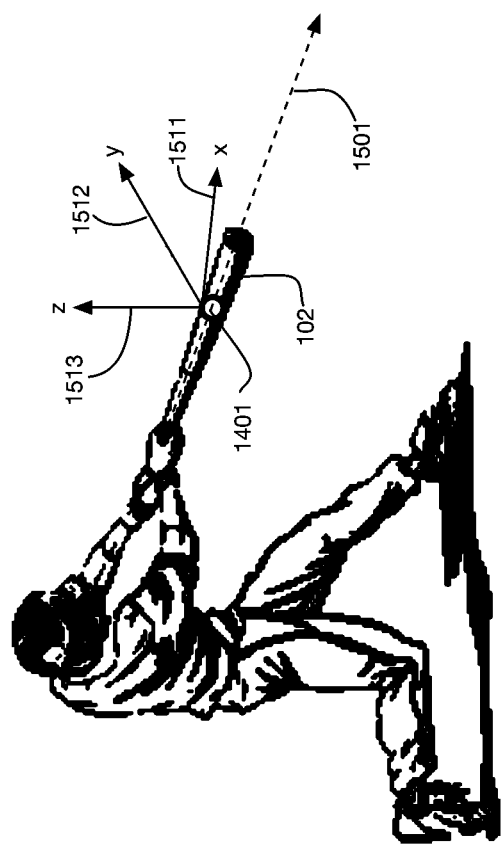
FIG. 15 illustrates a reference frame used in one or more embodiments to measure bat motion and to calculate swing metrics; this reference frame has the origin at the sweet spot, a vertical z-axis, and the bat is in the xz-plane at impact.

In one or more embodiments, data from sensor 104 may be integrated or otherwise analyzed to estimate the sensor velocity and position in an inertial (world) coordinate frame. The known position of the sweet spot relative to the sensor may then be used to calculate the sweet spot trajectory 1402 in this reference frame. In one or more embodiments, the world reference frame may be defined as illustrated in FIG. 15, which shows the bat at the point of impact with a ball (or at another point in time defined as a real or virtual time of impact). The origin of the reference frame is at the sweet spot of the bat 1401 at the moment of impact. Gravity is in the −z direction; hence the z axis 1513 points vertically upward. The world coordinate system is not based on an absolute horizontal reference point such as home plate or absolute north. Instead, the world frame is rotated so that the bat longitudinal axis 1501 is in the xz plane pointing in the +x direction 1511 (for right handed batters) or −x direction (for left-handed batters). The forward velocity of the bat is in the yz plane pointing in the +y direction 1512. Because of this definition, the actual orientation of the world coordinate frame will vary from swing to swing.

Figure 16:
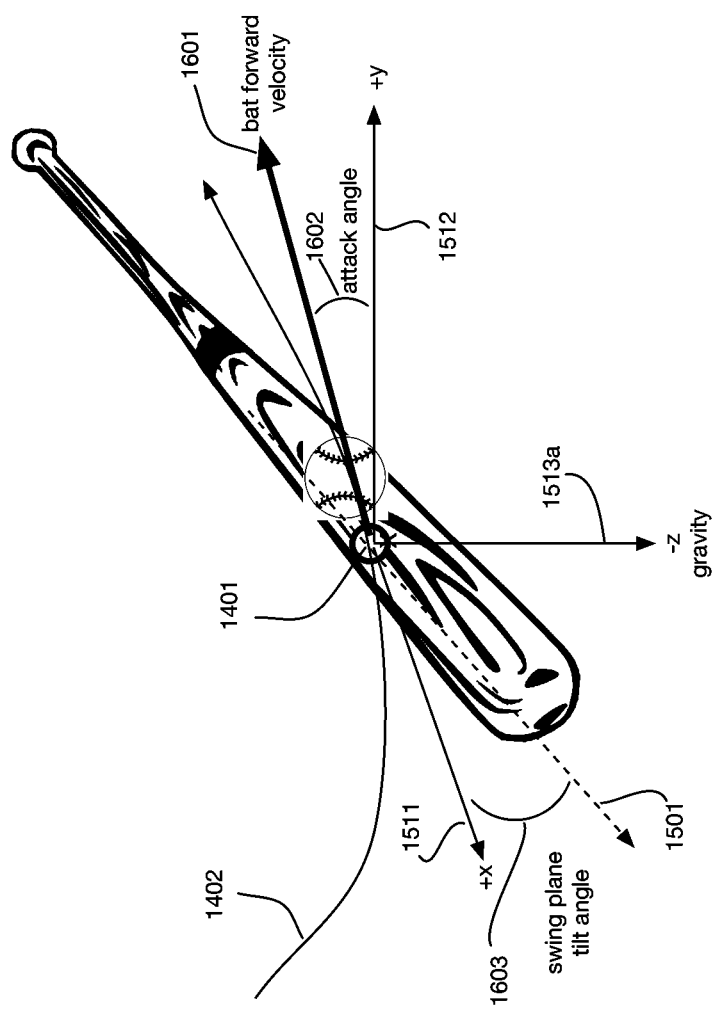
FIG. 16 shows another view of the reference frame of FIG. 15, and illustrates several swing metrics including the bat forward velocity at impact, the attack angle, and the swing plane tilt angle.

FIG. 16 shows a close-up view of the reference frame illustrated in FIG. 15, shown again at the point of impact of the swing. The reference frame origin is the location 1401 of the sweet spot of the bat at impact. The −z axis 1513a is in the direction of gravity, pointing vertically downward. Bat longitudinal axis 1501 is in the plane defined by the x axis 1511 and the −z axis 1513a. The y-axis 1512 is perpendicular to the x-axis and to the z-axis. In general, the bat may not be horizontally level at the time of impact; instead there may be a nonzero angle 1603 between the bat axis 1501 and the (horizontal) x-axis 1511, which is referred to as the vertical bat angle. Vertical bat angle is defined as the vertical direction of the bat with respect to horizontal at impact. Vertical bat angle is negative below horizontal and positive above horizontal. The swing plane tilt angle 1603 is the vertical bat angle at the moment of impact. The swing plane tilt angle is usually negative, meaning the bat is pointing toward the ground. A level bat would result in a swing plane tilt angle of 0°. Swing plane tilt angle is important for understanding adjustability and correlations to pitch types and locations. Pitch location will determine changes in the bat angle at impact. Adjusting the swing plane tilt angle to meet the pitch should be done early in the swing in order to achieve maximum efficiency. Adjustment later in the swing drains energy from the speed of the bat. The swing plane tilt angle should match the location of the pitch. Steeper angles are required for low, inside pitches, and shallower angles are required for high, outside pitches.

The velocity of the bat at impact may also in general not be horizontal; the attack angle 1602 is the angle of the bat's forward velocity at impact 1601 with respect to the horizontal y-axis 1512. Attack angle is negative below horizontal and positive above horizontal. A positive value indicates swinging up, and a negative value indicates swinging down, where zero is perfectly level. Attack angle is important for two reasons: First, matching the bat path to the pitch path increases the likelihood of contact. Because the pitch is thrown from an elevated mound, it is typically on a downward angle as it crosses the plate. Therefore, a positive attack angle provides more opportunity to execute against a variety of pitches, which vary in height, speed, and angle. Second, a positive attack angle will usually maximize launch distance, increasing the scoring value of the at-bat. The average fastball crosses the plate at a 6° downward angle, while an average breaking ball crosses the plate at 10°. Other factors include swing speed and style, pitch velocity and location, and game situation. Given the variation in incoming pitch descent angles and desired launch angle, the optimal attack angle is usually between +2° to +14° degrees. In a real game scenario, adaptation may be required to put the ball in play. The ideal attack angle results in the maximum distance for a given bat speed. For slow bat speeds, the ideal attack angle is around 21°, and it gets smaller with increasing speed. Discussions of ideal launch angle, exit speed, and scoring value appear for example in Nathan, "Optimizing the Swing," at www.hardballtimes.com/optimizing-the-swing, and in Arthur, "The New Science of Hitting," at www.fivethirtyeight.com/features/the-new-science-of-hitting.

The bat forward velocity 1601 is the projection of the velocity vector of the sweet spot onto the plane perpendicular to the bat longitudinal axis 1501; it ignores any speed in the direction of the bat axis 1501.

Figure 17:
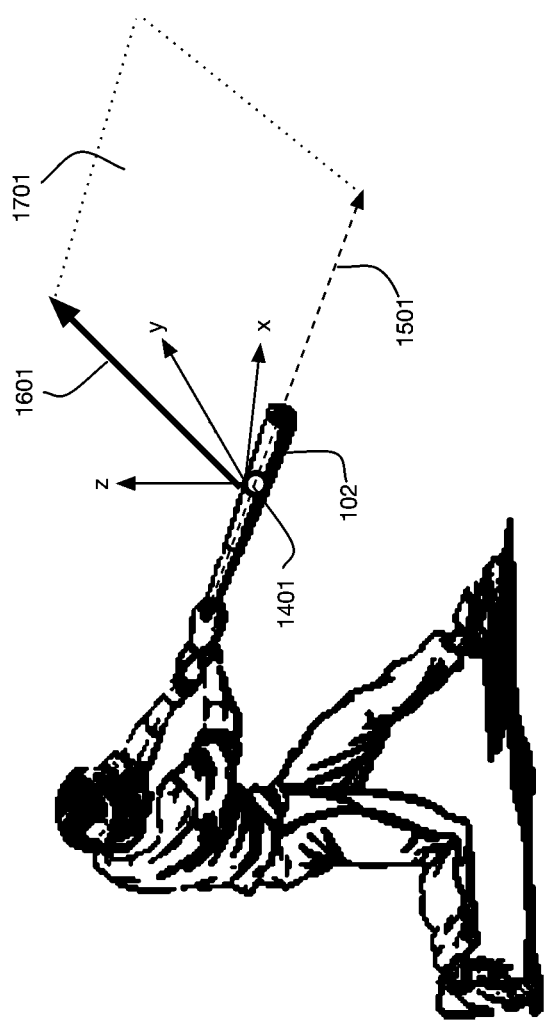
FIG. 17 shows a swing plane that is spanned by the bat's longitudinal axis and the velocity of the sweet spot at impact.

FIG. 17 illustrates a definition of a swing plane from which various swing metrics may be derived. Swing plane 1701 may for example be defined as a plane through the sweet spot 1401 which is spanned by the bat longitudinal axis 1501 at impact and by the bat forward velocity 1601 at impact. This swing plane is oriented so that it contains both the length of the bat and bat velocity at the moment of impact. The swing plane normal vector may found by normalizing the cross product of the bat length and bat velocity vectors. The normal vector is centered at the sweet spot of the bat at the moment of impact, i.e., at (0, 0, 0).

Figure 18:
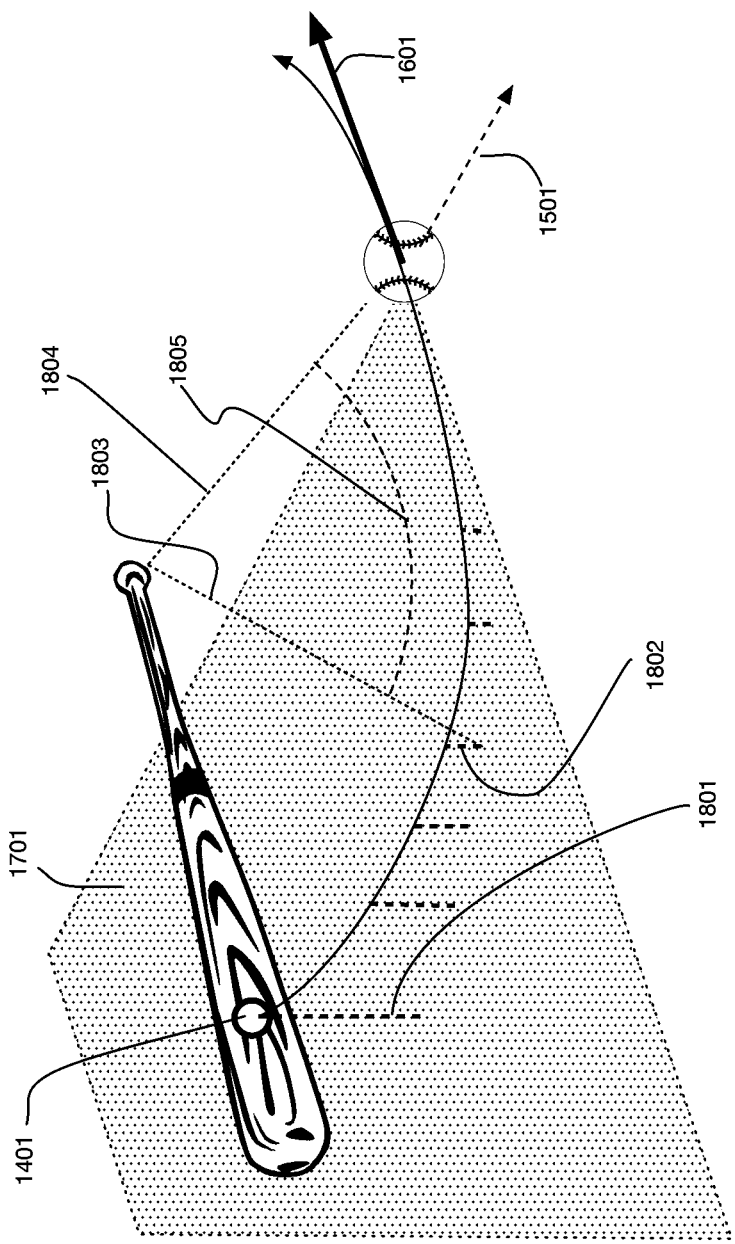
FIG. 18 shows the off-plane distance between the bat sweet spot and the swing plane during the swing, and it illustrates swing metrics that include the time when the bat is on-plane (within a specified threshold distance from the swing plane), and the on-plane metric that measures the angular range of motion while the bat is on-plane prior to impact.

A swing may be analyzed for example by decomposing the motion into swing plane versus off-plane components. Off-plane motion may for example be characterized by the distance of the sweet spot of the bat from the swing plane at any moment in time. FIG. 18 illustrates this distance of the sweet spot 1401 to the swing plane 1701 at several points in a swing prior to impact. For example, at the position of the bat shown in the figure, the off-plane distance is 1801. As the swing progresses towards impact, the sweet spot approaches more closely to the swing plane 1701. When the distance reaches a specified threshold 1802, the swing is considered "on-plane" at that moment (provided that it remains at or below this distance from that moment until impact). For example, the threshold may be set to 3 inches.

Based on the distance between the sweet spot and the swing plane, an on-plane metric may be defined as the total angular range of motion (for example in degrees) of the swing where the sweet spot of the bat is within the threshold value (such as three inches) from the swing plane. For example in FIG. 18 the on-plane metric is the angle 1805 between the ray 1803 at the on-plane event and the ray 1804 at the impact event. This metric measures an aspect of the quality of the swing because the player typically wants the energy from the body and arms to increase forward bat speed rather than change its direction. Changing bat direction takes more energy as bat speed increases, so an efficient swing gets on plane early and stays on plane as it approaches impact. Ideally, a batter will read the pitch early and adjust the entire body to align the swing plane with the pitch location. This enables maximum bat speed for every pitch type. In one or more embodiments, the system may report the percentage of total velocity that is generated while the bat in on plane. For example, if the velocity is 40% of the peak when the bat gets on plane, then the "on plane" metric is 60%.

Figure 19:
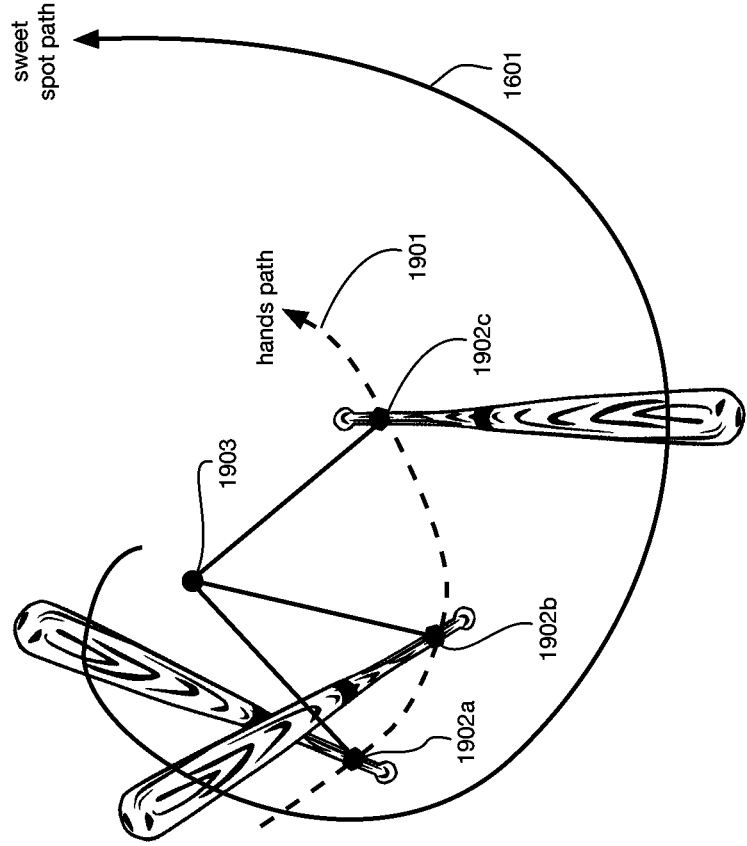
FIG. 19 illustrates an embodiment of a center of rotation calculation, which determines a point equidistant from the hand position on the bat at multiple points on the swing.

One or more embodiments may analyze the motion of a position on the bat where the hands grip the bat, in addition to or instead of analyzing the motion of the bat sweet spot. FIG. 19 illustrates an embodiment that determines a center of rotation 1903 for a swing by determining the position of the hands at three points in the swing, at location 1902a, 1902b, and 1902c. The center of rotation is selected for example as the point 1903 that is equidistant from these three points. One or more embodiments may use any point or points on hands trajectory 1901 to determine one or more centers of rotation for the swing. For example, point 1902a may be selected as the time when the xy magnitude of the gyroscope value from the sensor is at 50% of its impact value; point 1902b may be selected as the time when the xy magnitude of the gyroscope value is at 80% of its impact value; and point 1902c may be selected as the impact time. Using the hand positions at these times, the center of rotation may be calculated using the formula for the circumcenter of a triangle defined for example in en.wikipedia.org/wiki/Circumscribed_circle.

Three points on hands trajectory 1901 also define a plane, and therefore define an axis of rotation through the center of rotation 1903 that is perpendicular to that plane. The orientation of this axis of rotation may also be used in one or more embodiments as a metric describing the swing. The three points that define the center of rotation lie in a plane that is typically tilted downward in front of the body. The axis of rotation may be calculated for example using the cross product of any two of the radius vectors from the center of rotation calculation.

In one or more embodiments, a two-lever model may be used to describe and analyze a swing. During the early part of the downswing, an experienced batter rotates the core, arms, and bat as a single, connected unit. Then the batter commits by snapping the wrist, which moves the tip of the bat away from the body. The elbow may also extend, depending on ball location. This optimal kinematic sequence results in maximum speed and control.

The kinematic chain includes core, shoulder, elbow, and wrist rotation. In some situations, it may not be feasible to measure all these movements directly using, for example, a single inertial sensor on the bat. Instead, one or more embodiments may use a simplified two-lever mechanical model to distinguish "body" rotation from "bat" rotation. The body contribution ends at the hands. It measures rotation around the body center of rotation, which is primarily core, shoulder, and some elbow extension. The bat component measures motion around the hand position, which is primarily due to elbow and wrist rotation. In a connected swing, the shoulder and elbow contributions are small, and the body component of our model closely approximates core body rotation.

Figure 20:
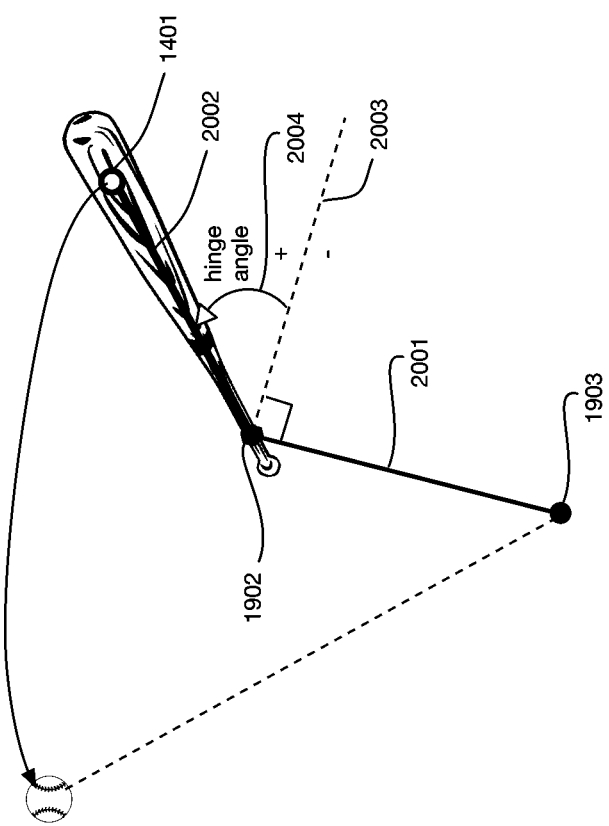
FIG. 20 illustrates a two-lever model of a swing that is used to calculate swing metrics such as a hinge angle between a bat lever and a body lever.

FIG. 20 illustrates a swing model that employs a simple two-lever mechanical system. This model focuses on the swing-plane and ignores any off-plane motion, which is characterized independently. The body lever is hinged at the body center of rotation and ends at the hand position. The bat lever is hinged at the hand position and extends along the axis of the bat. This model is illustrated in FIG. 20. Body lever 2001 extends from center of rotation 1903 to hand position 1902, and bat lever 2002 extends from hand position 1902 to sweet spot 1401.

Total bat speed is a combination of body rotation and bat rotation. The body ratio may be calculated the percentage of total rotation that is attributed to the body. An efficient swing uses both the body, arms, and wrists in the appropriate kinematic sequence. A swing that is mainly body rotation or mainly arm rotation is not as powerful as a swing that uses the entire kinematic chain. The body should contribute about 40% to 50% of the total rotational speed. There may be some variation due to individual style, but a value that is consistently outside this range usually indicates a poor kinematic sequence.

As the bat moves through the swing, the angle between the bat lever and the body lever changes. An angle that reflects the relative orientation of the bat lever and the body lever is called the hinge angle. In the illustrative embodiment shown in FIG. 20, the hinge angle 2004 is the angle between the bat lever 2002 and the tangent 2003 that is perpendicular to the body lever 2001 in the two-lever mechanical model. Hinge angle is negative when the tip of the bat is angled toward the body and positive when the tip is angled away from the body.

One or more embodiments may incorporate a method of calculating a commit event. The commit event, also known as wrist release, occurs when the hinge angle is "released". In other words, the moment when the hinge angle starts to move in a positive direction away from the body. Commit is the transition point in the kinematic chain between body-only motion and the wrist snap contribution. A batter begins the swing with the bat angled towards the body. At commit, this hinge angle is released and the wrist is snapped forward to add speed to the bat and to contact the ball.

Figure 21:
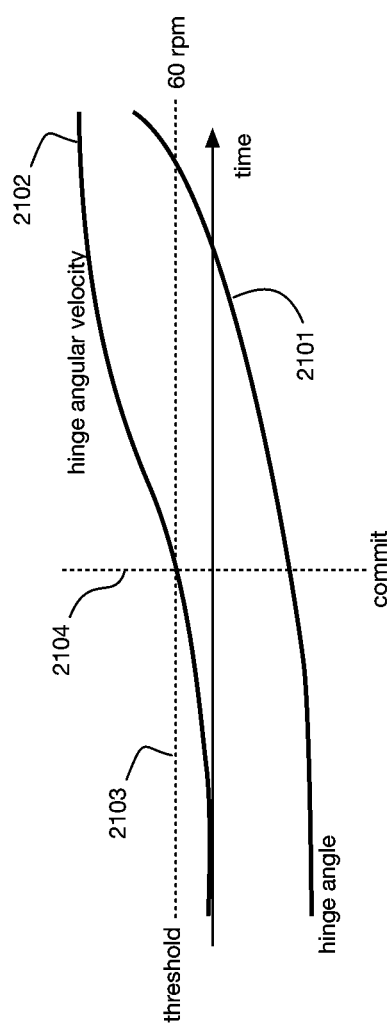
FIG. 21 shows a calculation of a commit event that may represent, for example, when the wrist snaps to release the bat from a cocked orientation to complete a swing.

FIG. 21 illustrates a method of calculating a commit event that may be used in one or more embodiments. The hinge angular velocity 2102 may be found by taking the first derivative of the hinge angle time series 2101. Any desired method may be used to calculate or estimate a derivative; for example, one or more embodiments may use a centered, five-sample window to reduce sample noise. The commit event 2104 may be defined as the instant when the hinge angular velocity 2102 exceeds a threshold value 2103 prior to impact. For example, a threshold value of 60 rpm (360 dps) is illustrated in FIG. 21.

Figure 22:
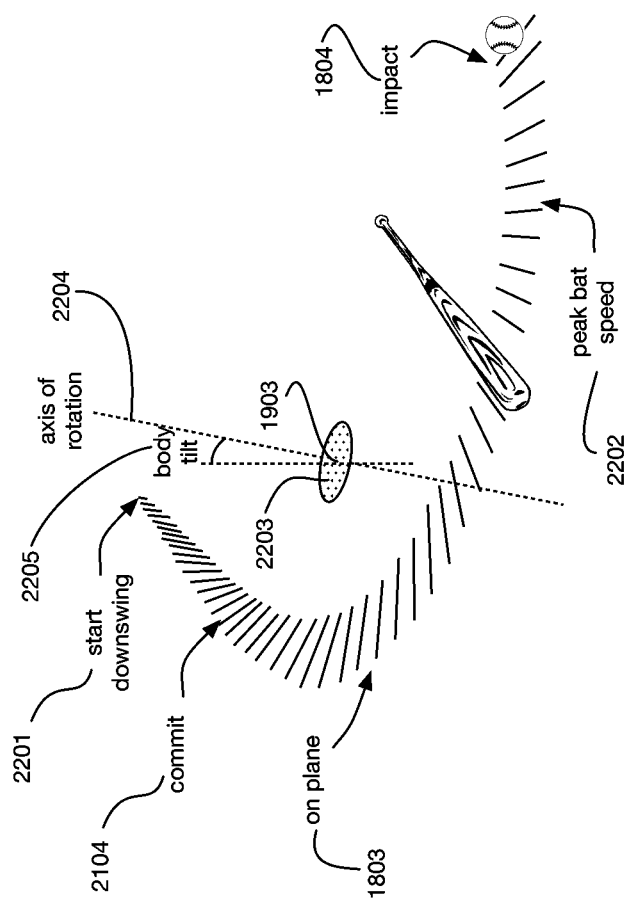
FIG. 22 shows an illustrative swing trajectory with several swing events annotated along the trajectory; it also illustrates a swing axis of rotation and a body tilt metric derived from this axis of rotation.

One or more embodiments may define a sequence of events through a swing, and may derive one or more metrics from these events. FIG. 22 shows an illustrative swing with events annotated at the point in the swing when they occur. Event 2201 is the start of the downswing of the swing. Start of downswing indicates the start of significant motion of the downswing. An illustrative algorithm that may be used in one or more embodiments to calculate the start of downswing is as follows. Start of downswing is calculated by looking at the gyro xy resultant time series. Starting from the peak value, work backwards one sample at a time. For each sample, fit a straight line through the peak value and the sample of interest. Find the moment in time where this straight-line approximation crosses through zero angular velocity. This is an estimate of the start of downswing.

Repeat this for every sample until the angular velocity of the sample of interest is less than 10% of the peak value. Keep the latest start of downswing estimate that was found during this search. This start of downswing algorithm uses the xy resultant, which is a better proxy for overall bat motion than, for example, using only the y component of motion. The model-based algorithm also provides more consistent estimates than a threshold-based or zero-crossing algorithm. By fitting a model to the overall shape of the angular velocity curve, the algorithm ignores meaningless hand motion near the start of downswing, where the signal is on the same order of magnitude as the noise. In one or more embodiments, the angular velocity curve is decomposed into two additive components, body lever and bat lever, and a metric is derived therefrom and optionally reported to the user and/or utilized for internal calculations. In some embodiments, other metrics may also be reported including measuring and comparing two parts (body and bat rotation) and utilizing peak speed ratios, amount of rotation ratios, peak angular velocity ratios, centripetal acceleration, i.e., how quickly a user starts accelerating a bat through body rotation to form metrics. Another metric may be formed by dividing peak hand speed by peak bat speed or an average of the hand speed and bat speed from commit to impact to reduce variability in the measurement. In one or more embodiments, any of these metrics or any other metrics defined herein may be provided to the user through sound, for example if over, equal to, or under a predetermined threshold, or via a visual display, or AR/VR/MR display (or through both audio and visual) to provide the user with biofeedback for use by the user to observe and/or alter position, posture, swing.

Commit event 2014, also known as wrist release, occurs when the hinge angle is released, as described with respect to FIG. 21.

The on-plane event 1803 occurs when the sweet spot approaches to within a threshold (such as three inches, for example) of the swing plane, as described with respect to FIG. 18.

For a swing that hits a ball, impact event 1804 occurs when the bat hits the ball and when this impact is detected by the sensor or sensors. One or more embodiments may also detect a virtual impact event even when the bat does not hit a ball (for example, for an "air swing"), as described below.

For embodiments with an accelerometer, a simple impact detection may be performed by searching for a large discontinuity in accelerometer readings, corresponding to the shock of the impact. However, certain batters generate accelerometer noise greater than 4g prior to true impact. This has been observed in internal testing and in pro-level swings. Analysis shows that this noise is almost always associated with high bat roll (z-axis angular velocity). Presumably, the bat is slipping in the grip, and the noise is caused by friction of the bat against the hands or gloves. Therefore, in one or more embodiments, the impact detection algorithm may use both the gyro and accelerometer to detect impact. The gyro search detects impact energy that is spread out over one or more subsequent samples. Searching forward, keep a running sum of the maximum gyro x, y, or z discontinuity. Reset the sum to zero if the discontinuity drops below 540 dps and remember that sample. Stop searching if the total discontinuity exceeds 1040 dps. The gyro-only impact is the last sample that was remembered.

Starting from the gyro-only impact sample, search backward until the accelerometer x, y, or z discontinuity is less than a threshold (80% of the saturation value). Usually, this occurs zero or one samples prior to the gyro-only impact, but sometimes it can more. Impact is defined as the sample just before the accelerometer discontinuity.

In rare cases, there is insufficient energy in the gyro signal to detect impact. In this case, impact is the defined as the sample just before the first accelerometer discontinuity that exceeds the threshold.

In one or more embodiments, air swings are supported by enabling an air swing version of the impact detection algorithm. If the system does not detect an impact event, the baseball swing processor determines whether the swing is a valid air swing. The air swing detection algorithm may for example look for peaks in the gyro xy resultant and accelerometer z component. A swing may be classified as a valid air swing if for example: the gyro xy peak exceeds 500 dps; the accelerometer z component peak exceeds 4 g; and the two peaks occur within 100 ms. In the case of a valid air swing, the time of the gyro xy peak may be used as a proxy for the impact event in all subsequent calculations. Processing of air swings continues the same as for impact swings. All swings may be considered invalid if the air swing criteria are not met, even if there is a valid impact signature.

Peak bat speed event 2202 occurs at the moment of maximum forward bat speed, which happens at or before the moment of impact. Peak bat speed is calculated using the forward bat speed time series. Working backwards from impact, peak bat speed is located by finding the sample with the peak value.

Average power generated during the swing may be calculated as power=mass×speed×acceleration, where mass is the effective mass of the bat, speed is the bat speed at impact, and acceleration is the average acceleration during the downswing (bat speed/time to contact). Power may be measured in Watts. The more mass the batter accelerates to high speed, the higher the power.

Based on the start of downswing event 2201 and the impact event 1804, a time to contact metric may be calculated as the elapsed time between start of downswing and impact. The clock starts when there is sufficient downswing motion and ends when the bat contacts the ball (or at a corresponding virtual impact event for an air swing). Time to contact measures the total time it takes to complete a swing. A major league fastball takes about 400 milliseconds from pitcher to home plate. In that time, the batter must recognize the pitch, decide whether to commit, and execute the swing. The quicker the time to contact, the more time the batter has to recognize and commit to good pitches. The ideal time to contact depends on age, strength, bat length and weight, experience level, and swing style. Our testing shows the typical time to contact for different age groups and skill levels: Little League: 230-400 milliseconds; Senior League: 185-325 milliseconds; High School: 140-260 milliseconds; College/Pro: 100-200 milliseconds.

FIG. 22 also illustrates metrics related to the orientation of the swing. For example, axis of rotation 2204, which is perpendicular to plane 2203 spanning points on the hand trajectory and is through center of rotation 1903, forms a body tilt angle 2205 with the vertical axis. The center of rotation is a point at the center of the arc traced by the hands and is usually near the body's center of rotation. The axis of rotation is the axis that the body rotates around and is usually aligned with the spine. The body tilt angle is the angle between the axis of rotation and vertical. The body and bat should rotate around the same axis. A large difference between the swing plane tilt angle and the body tilt angle is an indication of a disconnected swing. In an efficient swing, the swing plane tilt angle and body tilt angle should be closely-aligned.

Figure 23:
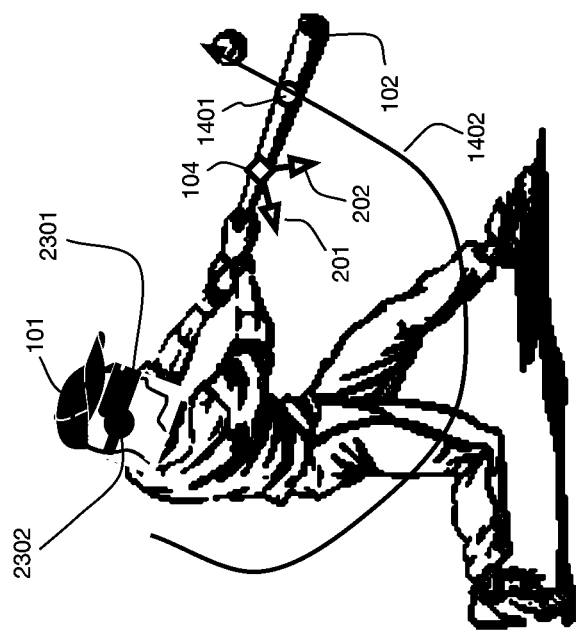
FIG. 23 shows an embodiment that provides bio-feedback to the user for setting posture or position or swing or any combination thereof via sound or AR/VR/MR visual displays, that enables working on postures, positions, swings and detecting proper or improper postures, positions, swings or portions thereof and to improve power and/or efficiency and to enable rehabilitation.

FIG. 23 shows an embodiment that provides bio-feedback to the user for setting posture or position or swing or any combination thereof via sound or AR/VR/MR visual displays, that enables working on postures, positions, swings and detecting proper or improper postures, positions, swings or portions thereof and to improve power and/or efficiency and to enable rehabilitation. One or more embodiments of the invention may include utilizing sound, e.g., via headphones 2302, or at least one Virtual Reality (VR), Augmented Reality (AR) or Mixed Reality (MR) display, glasses or goggles 2301 to provide bio-feedback to the user. In one or more embodiments the audio and/or image components 2301 and/or 2302 may be coupled with or formed into a helmet, such as a batter's helmet for example. This enables the user to see the pitch approach, wherein the headset tracks the ball coming to provide metrics, and after the ball is hit, the system provides the user with the hitting metrics and/or a 3D tracer overlay, for example of the swing. MR is also referred to as "hybrid reality" and includes use of real and virtual data to produce novel environments and visual displays that include real and computed objects and interact, which also may include real-time display of data. For example, in one or more embodiments, a sound or visual display may be utilized to provide feedback to the user to indicate a correct position, or movement has been achieved. This enables a user to work on portions of a swing or an entire swing using different body positions, for example to simulate different feet positions in a sand trap for a golf swing for example and obtain feedback regarding the position and/or swing using sound or visual feedback. In addition, by providing metrics regarding the body position, body movement, piece of equipment position, piece of equipment movement or any combination thereof, embodiments of the invention enable a user to work on developing more power and improving skills in a bio-feedback environment and/or combine environment. Embodiments of the system also enable rehabilitation and general training of the body based on the data gathered by the system to suggest areas of the body to strength or stretch to improve the range of motion to avoid injury through use of correct biomechanics.

While the ideas herein disclosed has been described by means of specific embodiments and applications thereof, numerous modifications and variations could be made thereto by those skilled in the art without departing from the scope of the invention set forth in the claims.

What is claimed is:

1. A swing analysis method using a sweet spot trajectory, comprising:
   obtaining a time series of sensor data from a sensor coupled to a piece of equipment during a swing of said piece of equipment, wherein said sensor comprises
      a three-axis accelerometer that generates acceleration data; and,
      a three-axis gyroscope that generates angular velocity data;
   determining a time of impact of said swing;
   obtaining a location of a sweet spot of said piece of equipment,
   defining a reference frame;
   calculating a trajectory of said sweet spot relative to said reference frame based on said sensor data; and,
   calculating one or more swing metrics based on said trajectory of said sweet spot and on said time of impact.

2. The method of claim 1 wherein said piece of equipment comprises a bat and wherein
   said sensor data comprises said acceleration data and said velocity data;
   said time of impact of said swing is determined from said time series of said sensor data;
   said sweet spot comprises a location on said piece of equipment at a distance between four inches and eight inches from a tip of said piece of equipment and,
   said reference frame is defined from said sensor data.

3. The method of claim 2 further comprising
   determining a forward bat velocity as a velocity of said sweet spot projected onto a plane perpendicular to a longitudinal axis of said bat, at one or more points in time during said swing.

4. The method of claim 3 wherein said one or more swing metrics comprise
   a bat speed, wherein said bat speed comprises a magnitude of said forward bat velocity at said time of impact.

5. The method of claim 4 wherein said one or more swing metrics comprise a swing power, wherein said swing power comprises a product of
   said bat speed, and
   a mass of said piece of equipment, and
   an average acceleration of said sweet spot during said swing.

6. The method of claim 3 wherein said one or more swing metrics comprise
   a peak bat speed, wherein said peak bat speed comprises a maximum magnitude of said forward bat velocity during said swing.

7. The method of claim 1 wherein said reference frame comprises
   an origin at a position of said sweet spot at said time of impact;
   a z-axis pointing vertically upward from said origin in a direction opposite to a gravity vector;
   an x-axis perpendicular to said z-axis and oriented so that a longitudinal axis of said piece of equipment lies in a plane defined by said z-axis and said x-axis at said time of impact; and,
   a y-axis perpendicular to said x-axis and to said z-axis.

8. The method of claim 7 wherein said determining said time of impact comprises
   determining whether said swing is a valid air swing; and,
   when said swing is said valid air swing, setting said time of impact to a time when a magnitude of said angular velocity data projected onto an xy-plane defined by said x-axis and said y-axis in said reference frame equals a peak value of said magnitude of said angular velocity data projected onto said xy-plane during said swing.

9. The method of claim 8 wherein said determining whether said swing is said valid air swing comprises
   determining whether said peak value of said magnitude of said angular velocity data projected onto said xy-plane exceeds a first threshold;
   calculating a peak value of a magnitude of said acceleration data projected onto said z-axis during said swing; and,
   determining whether said peak value of said magnitude of said acceleration data projected onto said z-axis exceeds a second threshold.

10. The method of claim 1 wherein said determining said time of impact comprises
    searching said time series of said sensor data for a change in said angular velocity data exceeding a first threshold; and, searching said time series of said sensor data for a change in said acceleration data exceeding a second threshold.

11. The method of claim 1 further comprising:
determining a time of start of downswing of said swing; and,
calculating a time to contact metric as a difference between said time of impact and said time of start of downswing.

12. The method of claim 1 further comprising:
calculating a trajectory of a hand position on said piece of equipment relative to said reference frame based on said sensor data.

13. The method of claim 12 further comprising:
calculating a center of rotation of said swing relative to said reference frame based on said sensor data.

14. The method of claim 13, wherein said calculating said center of rotation of said swing comprises
calculating said center of rotation as a point that is equidistant from said hand position at three different points of said trajectory of said hand position.

15. The method of claim 14, further comprising:
calculating an axis of rotation as an axis perpendicular to a plane through said three different points of said trajectory of said hand position.

16. The method of claim 15, wherein said one or more swing metrics comprises
a body tilt angle, wherein said body tilt angle comprises an angle between said axis of rotation and a vertical axis.

17. The method of claim 13 further comprising:
calculating a two-lever model of said swing based on
said trajectory of said sweet spot;
said trajectory of said hand position; and
said center of rotation; and,
wherein said calculating said one or more swing metrics is based on said two-lever model.

18. The method of claim 17 wherein said piece of equipment comprises a bat, and wherein said two-lever model comprises
a body lever extending from said center of rotation to said hand position; and
a bat lever extending from said hand position to said sweet spot.

19. The method of claim 18 wherein said one or more swing metrics comprise
a body ratio, wherein said body ratio comprises a ratio of a rotation of said body lever during said swing to a rotation of said bat lever during said swing.

20. The method of claim 18 wherein said one or more swing metrics comprise
a hinge angle based on a relative orientation between said bat lever and said body lever, at one or more points in time during said swing.

21. The method of claim 20 wherein said one or more swing metrics comprise
a hinge angle at impact, wherein said hinge angle at impact comprises said hinge angle at said time of impact.

22. The method of claim 20 wherein said one or more swing metrics comprise
a time of commit, wherein said time of commit is a point in time wherein a rate of change of said hinge angle exceeds a threshold.

23. The method of claim 22 wherein said one or more swing metrics comprise a hinge angle at commit, wherein said hinge angle at commit comprises said hinge angle at said time of commit.

24. The method of claim 20 wherein said one or more swing metrics comprise
a hinge angle at impact, wherein said hinge angle at impact comprises said hinge angle at said time of impact;
a time of commit, wherein said time of commit is a point in time wherein a rate of change of said hinge angle exceeds a threshold;
a hinge angle at commit, wherein said hinge angle at commit comprises said hinge angle at said time of commit; and,
a hinge release, wherein said hinge release comprises a difference between said hinge angle at impact and said hinge angle at commit.

25. The method of claim 1 wherein said piece of equipment comprises a bat, and further comprising
determining a bat impact velocity vector as a velocity of said sweet spot at said time of impact; and,
determining a swing plane as a plane through said sweet spot at said time of impact and spanned by said bat impact velocity vector and by a longitudinal axis of said piece of equipment at said time of impact.

26. The method of claim 25 further comprising
calculating an off-plane distance as a distance between said sweet spot and said swing plane, at one or more points in time during said swing.

27. The method of claim 26 further comprising
calculating a time on plane as an earliest time in said swing when said off-plane distance is below a threshold and remains below said threshold until said time of impact.

28. The method of claim 27 wherein said one or more swing metrics comprise
an on-plane metric, wherein said on-plane metric comprises an angular range of motion between said time on plane and said time of impact.

29. The method of claim 1 wherein said one or more swing metrics comprise
a swing plane tilt angle, wherein said swing plane tilt angle comprises an angle of a longitudinal axis of said piece of equipment with respect to horizontal at said time of impact, or
an attack angle, wherein said attack angle comprises an angle of a velocity vector of said sweet spot with respect to horizontal at said time of impact, or
both said swing plane tilt angle and said attack angle.

30. The method of claim 1 further comprising:
providing sound or image data based on said time series of sensor data, or providing metrics derived from said time series of sensor data.

* * * * *